US008420693B2

(12) United States Patent
Attardo et al.

(10) Patent No.: US 8,420,693 B2
(45) Date of Patent: Apr. 16, 2013

(54) DIPYRROLE COMPOUNDS, COMPOSITIONS, AND METHODS FOR TREATING CANCER OR VIRAL DISEASES

(75) Inventors: Giorgio Attardo, Laval (CA); Sasmita Triparthy, Montreal (CA); Elise Rioux, Montreal (CA); Gerson Gonzalez, Montreal (CA)

(73) Assignee: Gemin X Pharmaceuticals Canada Inc., Montreal, Quebec (CA)

( * ) Notice: Subject to any disclaimer, the term of this patent is extended or adjusted under 35 U.S.C. 154(b) by 762 days.

(21) Appl. No.: 11/794,488

(22) PCT Filed: Dec. 22, 2005

(86) PCT No.: PCT/CA2005/001955
§ 371 (c)(1),
(2), (4) Date: Jun. 2, 2008

(87) PCT Pub. No.: WO2006/069441
PCT Pub. Date: Jul. 6, 2006

(65) Prior Publication Data
US 2008/0280896 A1  Nov. 13, 2008

Related U.S. Application Data

(60) Provisional application No. 60/639,911, filed on Dec. 28, 2004.

(51) Int. Cl.
*A61K 31/40* (2006.01)
(52) U.S. Cl.
USPC .......................... 514/422; 514/424; 514/427
(58) Field of Classification Search .................. 514/422, 514/424, 427
See application file for complete search history.

(56) References Cited

U.S. PATENT DOCUMENTS

| 4,916,711 | A | 4/1990 | Boyer et al. |
|---|---|---|---|
| 5,189,029 | A | 2/1993 | Boyer et al. |
| 5,446,157 | A | 8/1995 | Morgan et al. |
| 5,948,593 | A | 9/1999 | Misawa et al. |
| 6,071,947 | A | 6/2000 | D'Alessio et al. |
| 6,369,096 | B1 | 4/2002 | D'Alessio et al. |
| 6,407,244 | B1 | 6/2002 | Murthy et al. |
| 6,602,879 | B2 | 8/2003 | Murthy et al. |
| 7,144,912 | B2 | 12/2006 | Johnson et al. |
| 2003/0082406 | A1 | 5/2003 | Murase et al. |
| 2004/0014987 | A1 | 1/2004 | Murthy et al. |
| 2005/0014802 | A1 | 1/2005 | Attardo et al. |
| 2006/0035945 | A1 | 2/2006 | Attardo et al. |
| 2007/0037856 | A1 | 2/2007 | Johnson et al. |

FOREIGN PATENT DOCUMENTS

| CA | 2 398 173 A1 | 1/2001 |
|---|---|---|
| CA | 2 453 636 A1 | 1/2003 |
| CA | 2 527 583 A1 | 12/2004 |
| EP | 0361936 | 1/1996 |
| EP | 0822544 | 1/2001 |
| JP | 11-256057 | 9/1999 |
| JP | 2001-223081 | 8/2001 |
| JP | 2001-223082 | 8/2001 |
| JP | 2001-257077 | 9/2001 |
| JP | 2001-297881 | 10/2001 |
| JP | 2001-307884 | 11/2001 |
| JP | 2002-38040 | 2/2002 |
| JP | 2002-134274 | 5/2002 |
| JP | 2003-151773 | 5/2003 |
| JP | 2004-200162 | 7/2004 |
| WO | WO-98/40380 | 9/1998 |
| WO | WO-99/40069 A1 | 8/1999 |
| WO | WO-2004/046151 | 6/2004 |
| WO | WO-2004/053459 | 6/2004 |

OTHER PUBLICATIONS

International Search Report issued for International Patent Application No. PCT/CA2005/001955.
Melvin et al, "Double-Strand DNA cleavage by Copper-Prodigiosin," J.Am. Chem. Soc., vol. 122, pp. 6333-6334 (2000).
Melvin et al., "Influence of the A-Ring on the Redox and Nuclease Properties of the Prodigiosins: Importance of the Bipyrrole moiety in Oxidative DNA Cleavage," Chem. Res. Toxicol, vol. 15, pp. 742-748 (2002).
Morgan et al., "Pentamethylpyrromethene boron difluoride complexes in human ovarian cancer photodynamic therapy," SPIE vol. 1203, pp. 253-265 (1990).
Woodburn et al., "Biodistribution and PDT efficacy of ketochlorin photosensitzer as function of the delivery vehicle," Photochemistry and Photobiology, vol. 60, pp. 154-159 (1994).
Xu et al., "Multiphoton excitation cross-sections of molecular fluorophores," Bioimaging, vol. 4, 198-207 (1996).

*Primary Examiner* — James D Anderson
(74) *Attorney, Agent, or Firm* — Wilmer Cutler Pickering Hale and Dorr LLP

(57) ABSTRACT

The present invention relates to novel Dipyrrole Compounds, compositions comprising a Dipyrrole Compound, and methods useful for treating or preventing cancer or a neoplastic disorder comprising administering a Dipyrrole Compound. The compounds, compositions, and methods of the invention are also useful for inhibiting the growth of a cancer cell or neoplastic cell, treating or preventing a viral infection, or inhibiting the replication and/or infectivity of a virus. The invention also provides screening assays for compounds that can be used in combination with Dipyrrole Compounds for the treatment of cancer or neoplastic disease, inhibition of cancer cell growth, or treatment of viral infections.

15 Claims, 3 Drawing Sheets

US 8,420,693 B2

DIPYRROLE COMPOUNDS, COMPOSITIONS, AND METHODS FOR TREATING CANCER OR VIRAL DISEASES

This application is the U.S. National Stage of International Application No. PCT/CA2005/001955, filed Dec. 22, 2005, which claims the benefit of U.S. Provisional Application No. 60/639,911, filed Dec. 28, 2004, the disclosure of each of which is incorporated by reference herein in its entirety.

1. FIELD OF THE INVENTION

The present invention relates to Dipyrrole Compounds, compositions comprising a Dipyrrole Compound, and methods useful for treating or preventing cancer or a neoplastic disorder comprising administering an effective amount of a Dipyrrole Compound. The compounds, compositions, and methods of the invention are also useful for treating or preventing cancer or neoplastic disease, or inhibiting the growth of a cancer cell or neoplastic cell, treating or preventing a viral infection, or inhibiting the replication or infectivity of a virus. The invention also provides screening assays for compounds that can be used in combination with Dipyrrole Compounds for the treatment of cancer or neoplastic disease, inhibition of cancer cell growth, or treatment of viral infections.

2. BACKGROUND OF THE INVENTION

2.1 Cancer and Neoplastic Disease

Cancer affects approximately 20 million adults and children worldwide, and this year, more than 9 million new cases will be diagnosed (International Agency for Research on Cancer; www.irac.fr). According to the American Cancer Society, about 563,100 Americans are expected to die of cancer this year, more than 1500 people a day. Since 1990, in the United States alone, nearly five million lives have been lost to cancer, and approximately 12 million new cases have been diagnosed.

Currently, cancer therapy involves surgery, chemotherapy and/or radiation treatment to eradicate neoplastic cells in a patient (see, for example, Stockdale, 1998, "Principles of Cancer Patient Management", in *Scientific American: Medicine*, vol. 3, Rubenstein and Federman, eds., Chapter 12, Section IV). All of these approaches pose significant drawbacks for the patient. Surgery, for example, may be contraindicated due to the health of the patient or may be unacceptable to the patient. Additionally, surgery may not completely remove the neoplastic tissue. Radiation therapy is effective only when the irradiated neoplastic tissue exhibits a higher sensitivity to radiation than normal tissue, and radiation therapy can also often elicit serious side effects. (Id.) With respect to chemotherapy, there are a variety of chemotherapeutic agents available for treatment of neoplastic disease. However, despite the availability of a variety of chemotherapeutic agents, chemotherapy has many drawbacks (see, for example, Stockdale, 1998, "Principles Of Cancer Patient Management" in *Scientific American Medicine*, vol. 3, Rubenstein and Federman, eds., ch. 12, sect. 10). Almost all chemotherapeutic agents are toxic, and chemotherapy causes significant, and often dangerous, side effects, including severe nausea, bone marrow depression, immunosuppression, etc. Additionally, many tumor cells are resistant or develop resistance to chemotherapeutic agents through multi-drug resistance.

Therefore, there is a significant need in the art for novel compounds and compositions, and methods that are useful for treating cancer or neoplastic disease with reduced or without the aforementioned side effects. Further, there is a need for cancer treatments that provide cancer-cell-specific therapies with increased specificity and decreased toxicity.

2.2 Viruses and Disease

In addition to cancer, an enormous number of human and animal diseases result from virulent and opportunistic viral infections (see Belshe (Ed.) 1984 *Textbook of Human Virology*, PSG Publishing, Littleton, Mass.). Viral diseases of a wide array of tissues, including the respiratory tract, CNS, skin, genitourinary tract, eyes, ears, immune system, gastrointestinal tract, and musculoskeletal system, affect a vast number of humans of all ages (see Table 328-2 In: Wyngaarden and Smith, 1988, *Cecil Textbook of Medicine*, 18$^{th}$ Ed., W.B. Saunders Co., Philadelphia, pp. 1750-1753).

Although considerable effort has been invested in the design of effective anti-viral therapies, viral infections continue to threaten the lives of millions of people worldwide. In general, attempts to develop anti-viral drugs have focused on several stages of viral life cycle (See e.g., Mitsuya, H., et al., 1991, FASEB J. 5:2369-2381, discussing HIV). However, a common drawback associated with using of many current anti-viral drugs is their deleterious side effects, such as toxicity to the host or resistance by certain viral strains.

Accordingly, there is a need in the art for anti-viral compounds, compositions, and methods that allow for safe and effective treatment of viral disease without the above-mentioned disadvantages.

Citation or identification of any reference in Section 2 of this application is not an admission that such reference is available as prior art to the present invention.

3. SUMMARY OF THE INVENTION

The present invention provides a method for treating cancer in a patient, wherein the method comprises administering to a patient in need thereof an effective amount of a Dipyrrole Compound of Formula (Ia):

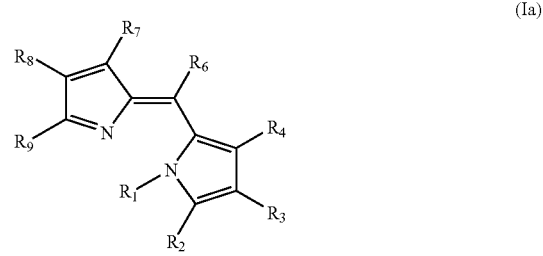

(Ia)

or a pharmaceutically acceptable salt thereof
wherein
$R_1$ is —H, —$C_1$-$C_8$ alkyl or —OH;
$R_2$ is —H, halogen, —$NH_2$, —CN, —$NO_2$, —$N_3$, —COOH, —C(O)$NH_2$, —SH, —S(O)$NH_2$, —S(O)$_2NH_2$, —$C_{11}$-$C_{10}$ (oxy)alkyl, —$C_1$-$C_{10}$ alkyl, —$C_1$-$C_{10}$ alkoxy, —$C_1$-$C_{10}$ (hydroxy)alkyl, —$C_1$-$C_{10}$ (amino)alkyl, —$C_2$-$C_{10}$ alkenyl, —$C_2$-$C_{10}$ alkynyl, —($C_3$-$C_7$) cycloalkyl, -aryl, —$C_1$-$C_{10}$ (aryl)alkyl, 3- to 12-membered heterocycle, —$OR_{12}$, —$CH_2OR_{10}$, —O($CH_2$)$_nOR_{10}$, —C(O)$R_{10}$, —O—C(O)$R_{10}$, —C(O)($CH_2$), —$R_{10}$, —O—C(O)$OR_{10}$, —O—C(O)$NHR_{10}$, —O—C(O)N($R_{10}$)$_2$, —C(O)N($R_{10}$)$_2$, —C(O)$OR_{10}$, —C(O)$NHR_{10}$, —S—$R_{10}$, —$SOR_{10}$, —S(O)$_2R_{10}$, —S(O)$_2NHR_{10}$, —NHC(O)$R_{10}$, —$NHSR_{10}$, —NH- $-SOR_{10}$, $-NHS(O)_2R_{10}$, $O-C(S)R_{10}$, $O-C(S)OR_{10}$, $O-C(S)NHR_{10}$, $O-C(S)N(R_{10})_2$, $-C(S)OR_{10}$, $-C(S)NHR_{10}$, $-C(S)N(R_{10})_2$, $-NHC(S)R_{10}$, $-NR_{10}C(S)R_{10}$, $-NHC(S)NHR_{10}$, $-NHC(S)N(R_{10})_2$, $-NR_{10}C(S)NHR_{10}$, $-NR_{10}C(S)N(R_{10})_2$ or $R_2$ and $R_3$, together with the carbon atom to which each is attached, join to form a 5- to 9-membered ring;

$R_3$ and $R_4$ are independently $-H$, halogen, $-NH_2$, $-CN$, $-NO_2$, $-N_3$, $-COOH$, $-C(O)NH_2$, $-SH$, $-S(O)NH_2$, $-S(O)_2NH_2$, $-C_1-C_{10}$ (oxy)alkyl, $-C_1-C_{10}$ alkyl, $-C_1-C_{10}$ alkoxy, $-C_1-C_{10}$ (hydroxy)alkyl, $-C_1-C_{10}$ (amino) alkyl, $-C_2-C_{10}$ alkenyl, $-C_2-C_{10}$ alkynyl, $-(C_3-C_7)$ cycloalkyl, -aryl, $-C_1-C_{10}$ (aryl)alkyl, 3- to 12-membered heterocycle, $-OR_{10}$, $-CH_2OR_{10}$, $-O(CH_2)_nR_{10}$, $-C(O)R_{10}$, $-O-C(O)R_{10}$, $-C(O)(CH_2)>-R_{10}$, $-O-C(O)OR_{10}$, $-O-C(O)NHR_{10}$, $-O-C(O)N(R_{10})_2$, $-C(O)N(R_{10})_2$, $-C(O)OR_{10}$, $-C(O)NHR_{10}$, $-S-R_{10}$, $-SOR_{10}$, $-S(O)_2R_{10}$, $-S(O)_2NHR_{10}$, $-NHC(O)R_{10}$, $-NHSR_{10}$, $-NHSOR_{10}$, $-NHS(O)_2R_{10}$, $O-C(S)R_{10}$, $O-C(S)OR_{10}$, $O-C(S)NHR_{10}$, $O-C(S)N(R_{10})_2$, $-C(S)OR_{10}$, $-C(S)NHR_{10}$, $-C(S)N(R_{10})_2$, $-NHC(S)R_{10}$, $-NR_{10}C(S)R_{10}$, $-NHC(S)NHR_{10}$, $-NHC(S)N(R_{10})_2$, $-NR_{10}C(S)NHR_{10}$, $-NR_{10}C(S)N(R_{10})_2$ or $R_2$ and $R_3$, or $R_3$ and $R_4$, together with the carbon atom to which each is attached, join to form a 5- to 9-membered ring;

$R_6$ is $-H$, halogen, $-OH$, $-NH_2$, $-C_1-C_8$ alkyl, or $-O-(C_1-C_8$ alkyl);

$R_7$ and $R_8$ are independently $-H$, $-OH$, halogen, amino, $-NH(C_1-C_5$ alkyl), $-N(C_1-C_5$ alkyl)$_2$, $-NH$(phenyl), $-N$(phenyl)$_2$, $-NH$(naphthyl), $-N$(naphthyl)$_2$, $-CN$, $-NO_2$, $-N_3$, $-C_1-C_8$ alkyl, $-O-(C_1-C_8$ alkyl), $-(C_1-C_8$ alkyl)-OH, $-O$-benzyl, $-C_2-C_8$ alkenyl, $-C_2-C_8$ alkynyl, $-C_3-C_{12}$ cycloalkyl, -phenyl, -naphthyl, -3- to 12-membered heterocycle, $-OR_{10}$, $-CH_2OR_{10}$, $-O(CH_2)_nR_{10}$, $-O(CH_2)_nOR_{10}$, $-CH_2-O-(CH_2)_nOR_{10}$, $-O-C(O)R_{10}$, $-C(O)(CH_2)_n-R_{10}$, $-C(O)R_{10}$, $-O-C(O)OR_{10}$, $-O-C(O)NHR_{10}$, $-O-C(O)N(R_{10})_2$, $-C(O)N(R_{10})_2$, $-C(O)OR_{10}$, $-C(O)NHR_{10}$, $-S-R_{10}$, $-SOR_{10}$, $-S(O)_2R_{10}$, $-NHC(O)R_{10}$, $-NHSR_{10}$, $-NHSOR_{10}$, $-NHS(O)_2R_{10}$, $O-C(S)R_{10}$, $O-C(S)OR_{10}$, $O-C(S)NHR_{10}$, $O-C(S)N(R_{10})_2$, $-C(S)OR_{10}$, $-C(S)NHR_{10}$, $-C(S)N(R_{10})_2$, $-NHC(S)R_{10}$, $-NR_{10}C(S)R_{14}$, $-NHC(S)NHR_{10}$, $-NHC(S)NHR_{10})_2$, $-NR_{10}C(S)NHR_{10}$, $-NR_{10}C(S)N(R_{10})_2$;

$R_9$ is $-(C_1-C_{10})$ alkyl, $-(C_3-C_{12})$ cycloalkyl, -aryl, $-C_1-C_{10}$ (aryl)alkyl, 3- to 12-membered heterocycle;

with the proviso that $R_2$, $R_3$, $R_4$, $R_7$, $R_8$ or $R_9$ is not pyrrole or indole;

each $R_{10}$ is independently $-H$, $-C_1-C_8$ alkyl, $-C_3-C_{12}$ cycloalkyl, -aryl, -3- to 12-membered heterocycle, $-C_2-C_8$ alkenyl, or $-C_2-C_8$ alkynyl;

$R_{12}$ is $-C_1-C_8$ alkyl, $-C_3-C_{12}$ cycloalkyl, -aryl, -3- to 12-membered heterocycle, $-C_2-C_8$ alkenyl, or $-C_2-C_8$ alkynyl;

each n is independently an integer ranging from 0 to 6;
wherein
when $R_2$ is ethyl, $R_4$ is other than $-H$, or
when $R_9$ is ethyl, $R_7$ is other than $-H$.

In certain specific embodiments, n is an integer from 1 to 6.

In certain specific embodiments, $R_9$ in Formula (Ia) is selected from the group consisting of aryl and a 3- to 12-membered heterocycle with the proviso that $R_9$ is not pyrrole or indole.

In certain specific embodiments, $R_7$ in Formula (Ia) is $-O-(C_1-C_8$ alkyl).

In certain specific embodiments, $R_7$ in Formula (Ia) is $-OCH_3$.

In certain specific embodiments, $R_7$ in Formula (Ia) is $-O-(C_1-C_8$ alkyl) optionally substituted by phenyl.

In certain specific embodiments, $R_7$ in Formula (Ia) is $-O$-benzyl.

In certain specific embodiments, the $-O$-benzyl in Formula (Ia) is unsubstituted.

In certain specific embodiments, $R_2$ and $R_4$ in Formula (Ia) are independently $C_1-C_{10}$ alkyl.

In certain specific embodiments, $R_2$ and $R_4$ in Formula (Ia) are both $-CH_3$. In certain specific embodiments, $R_2$ and $R_4$ in Formula (Ia) are both $-CH_3$ and $R_3$ in Formula (Ia) is $-H$.

In certain specific embodiments, $R_3$ in Formula (Ia) is $-H$.
In certain specific embodiments, $R_8$ in Formula (Ia) is $-H$.
In certain specific embodiments, $R_1$ in Formula (Ia) is $-H$.

In certain specific embodiments, $R_9$ in Formula (Ia) is aryl selected from substituted and unsubstituted phenyl, anthryl, fluorenyl, indenyl, azulenyl, phenanthryl and naphthyl.

In certain specific embodiments, $R_9$ is a 3- to 12-membered heterocycle selected from the group consisting of substituted and unsubstituted aziridinyl, oxiranyl, thiiranyl, aziranyl, diaziridinyl, diazirinyl, oxaziridinyl, azetidinyl, azetidinonyl, oxetanyl, thietanyl, piperidinyl, piperazinyl, morpholinyl, oxazinyl, thiazinyl, diazinyl, triazinyl, tetrazinyl, imidazolyl, benzimidazolyl, tetrazolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzothiazolyl, thiophenyl, pyrazolyl, triazolyl, benzodiazolyl, benzotriazolyl, pyrimidinyl, isoindolyl, indazolyl, benzothiophene, benzodioxole, dibenzofuran and dibenzothiophene.

In certain embodiments, $BF_3$ adducts are not salts within the scope of the invention.

In certain embodiments, $R_1$ and the pyrrole ring N atoms in Formula Ia do not form a third ring structure.

In certain embodiments, when $R_2$ in Formula Ia is $C_{1-10}$ alkyl then $R_4$ in Formula Ia is other than $-H$. In certain embodiments, when $R_9$ in Formula Ia is $C_{1-10}$ alkyl then $R_7$ in Formula Ia is other than $-H$.

The invention also provides a method for treating cancer or a neoplastic disease in a subject in need of treatment of cancer or a neoplastic disease, wherein the method comprises administering to the subject (i) an effective amount of compound of Formula (Ia) or a pharmaceutically acceptable salt thereof; and (ii) a pharmaceutically acceptable carrier. The invention also provides a method for treating cancer or a neoplastic disease in a subject in need of treatment of cancer or a neoplastic disease, wherein the method comprises administering to the subject (i) an effective amount of compound of Formula (Ia) or a pharmaceutically acceptable salt thereof; (ii) a pharmaceutically acceptable carrier; and (iii) a therapeutic agent other than a compound of Formula (Ia), such as another chemotherapeutic agent. Combinations of different compounds of Formula (Ia) may also be administered to treat the cancer or the neoplastic disease.

The invention provides methods for inhibiting or reducing the growth of a cancer cell or neoplastic cell, wherein the method comprises contacting the cancer cell or the neoplastic cell with an effective amount of compound of Formula (Ia) or a pharmaceutically acceptable salt thereof.

The invention further provides a method for treating a viral infection in a subject in need of treatment of a viral infection, wherein the method comprises administering to the subject (i) an effective amount of compound of Formula (Ia) or a pharmaceutically acceptable salt thereof; and (ii) a pharmaceutically acceptable carrier. The invention also provides a method for treating a viral infection in a subject in need of treatment of a viral infection, wherein the method comprises administering to the subject (i) an effective amount of compound of Formula (Ia) or a pharmaceutically acceptable salt thereof;

(ii) a pharmaceutically acceptable carrier; and (iii) a therapeutic agent other than a compound of Formula (Ia), such as another antiviral agent. Combinations of different compounds of Formula (Ia) may also be administered to treat viral infections.

The invention also provides methods for inhibiting or reducing the replication or infectivity of a virus, wherein the method comprises contacting a cell infected with the virus with an effective amount of compound of Formula (Ia) or a pharmaceutically acceptable salt thereof. The invention also provides methods for inhibiting or reducing the propagation of a virus-infected cell, wherein the method comprises contacting the virus-infected cell with an effective amount of compound of Formula (Ia) or a pharmaceutically acceptable salt thereof.

In certain specific embodiments, the invention provides a method for the treatment of cancer or a neoplastic disease in a subject in need of treatment of cancer or neoplastic disease, wherein the method comprises administering a Dipyrrole compound of Formula (Ib)

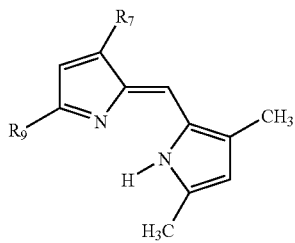

Ib wherein
$R_9$ is —$(C_3-C_{12})$ cycloalkyl, -aryl, —$C_1-C_{10}$ (aryl)alkyl, -3- to 12-membered heterocycle, with the proviso that $R_9$ is not pyrrole or indole; and
$R_7$ is —O—$(C_1-C_8$ alkyl) or —$OR_{11}$, wherein $R_{11}$ is aryl.

In certain specific embodiments, $R_9$ in Formula (Ib) is aryl or a 3- to 12-membered heterocycle, with the proviso that $R_9$ is not pyrrole or indole. In a specific embodiment, $R_7$ is methoxy.

In certain specific embodiments, $R_9$ in Formula (Ib) is selected from the group consisting of substituted and unsubstituted phenyl, quinolinyl, thienyl, benzothiophenyl, furyl, napthyl, pyridinyl, dihydrobenzofuranyl, pyrimidinyl, dihydrooxazinylphenyl, and pyrazolyl.

The invention also provides a method for treating cancer or a neoplastic disease in a subject in need of treatment of cancer or a neoplastic disease, wherein the method comprises administering to the subject (i) an effective amount of compound of Formula (Ib) or a pharmaceutically acceptable salt thereof; and (ii) a pharmaceutically acceptable carrier. The invention also provides a method for treating cancer or a neoplastic disease in a subject in need of treatment of cancer or a neoplastic disease, wherein the method comprises administering to the subject (i) an effective amount of compound of Formula (Ib) or a pharmaceutically acceptable salt thereof; (ii) a pharmaceutically acceptable carrier; and (iii) a therapeutic agent other than a compound of Formula (Ib), such as another chemotherapeutic agent. Combinations of different compounds of Formula (Ib) may also be administered to treat the cancer or the neoplastic disease.

The invention provides methods for inhibiting or reducing the growth of a cancer cell or neoplastic cell, wherein the method comprises contacting the cancer cell or the neoplastic cell with an effective amount of compound of Formula (Ib) or a pharmaceutically acceptable salt thereof.

The invention further provides a method for treating a viral infection in a subject in need of treatment of a viral infection, wherein the method comprises administering to the subject (i) an effective amount of compound of Formula (Ib) or a pharmaceutically acceptable salt thereof; and (ii) a pharmaceutically acceptable carrier. The invention also provides a method for treating a viral infection in a subject in need of treatment of a viral infection, wherein the method comprises administering to the subject (i) an effective amount of compound of Formula (Ib) or a pharmaceutically acceptable salt thereof; (ii) a pharmaceutically acceptable carrier; and (iii) a therapeutic agent other than a compound of Formula (Ib); such as another antiviral agent. Combinations of different compounds of Formula (Ib) may also be administered to treat viral infections.

The invention also provides methods for inhibiting or reducing the replication or infectivity of a virus, wherein the method comprises contacting a cell infected with the virus with an effective amount of compound of Formula (Ib) or a pharmaceutically acceptable salt thereof. The invention also provides methods for inhibiting or reducing the propagation of a virus-infected cell, wherein the method comprises contacting the virus-infected cell with an effective amount of compound of Formula (Ib) or a pharmaceutically acceptable salt thereof.

In certain specific embodiments, the invention provides a method for the treatment of cancer or a neoplastic disease in a subject in need of treatment of cancer or neoplastic disease, wherein the method comprises administering an effective amount of:
3-methoxy-2-((3,5-dimethyl-1H-pyrrol-2-yl)methylene)-5-phenyl-2H-pyrrole [Compound 1];
5-(4-chlorophenyl)-3-methoxy-2-((3,5-dimethyl-1H-pyrrol-2-yl)methylene)-2H-pyrrole [Compound 2];
2-((5-(2,4-difluorophenyl)-3-methoxy-2H-pyrrol-2-ylidene)methyl)-3,5-dimethyl-1H-pyrrole [Compound 3];
5-(4-methoxy-5-((3,5-dimethyl-1H-pyrrol-2-yl)methylene)-5H-pyrrol-2-yl)quinoline [Compound 4];
5-(4-fluorophenyl)-3-methoxy-2-((3,5-dimethyl-1H-pyrrol-2-yl)methylene)-2H-pyrrole [Compound 5];
2-((3-methoxy-5-(thiophen-2-yl)-2H-pyrrol-2-ylidene)methyl)-3,5-dimethyl-1H-pyrrole [Compound 6];
2-((5-(5-bromothiophen-2-yl)-3-methoxy-2H-pyrrol-2-ylidene)methyl)-3,5-dimethyl-1H-pyrrole [Compound 7];
N-4-(4-methoxy-5-((3,5-dimethyl-1H-pyrrol-2-yl)methylene)-5H-pyrrol-2-yl)-phenyl-methylsulfonamide [Compound 8];
4-(4-methoxy-5-((3,5-dimethyl-1H-pyrrol-2-yl)methylene)-5H-pyrrol-2-yl)benzaldehyde [Compound 9];
2-((5-(benzo[b]thiophen-2-yl)-3-methoxy-2H-pyrrol-2-ylidene)methyl)-3,5-dimethyl-1H-pyrrole [Compound 10];
5-methoxy-2-(4-methoxy-5-((3,5-dimethyl-1H-pyrrol-2-yl)methylene)-5H-pyrrol-2-yl)benzaldehyde [Compound 11];
2-((3-methoxy-5-(3-nitrophenyl)-2H-pyrrol-2-ylidene)methyl)-3,5-dimethyl-1H-pyrrole [Compound 12];
2-((5-(furan-2-yl)-3-methoxy-2H-pyrrol-2-ylidene)methyl)-3,5-dimethyl-1H-pyrrole [Compound 13];
2-((5-(furan-3-yl)-3-methoxy-2H-pyrrol-2-ylidene)methyl)-3,5-dimethyl-1H-pyrrole [Compound 14];
2-((3-methoxy-5-(thiophen-3-yl)-2H-pyrrol-2-ylidene)methyl)-3,5-dimethyl-1H-pyrrole [Compound 15];

2-((3-methoxy-5-(2,4-dimethoxyphenyl)-2H-pyrrol-2-ylidene)methyl)-3,5-dimethyl-1H-pyrrole [Compound 16];

2-((3-methoxy-5-(3,4-dimethoxyphenyl)-2H-pyrrol-2-ylidene)methyl)-3,5-dimethyl-1H-pyrrole [Compound 17];

2-((3-methoxy-5-(2,3,4-trimethoxyphenyl)-2H-pyrrol-2-ylidene)methyl)-3,5-dimethyl-1H-pyrrole [Compound 18];

2-((3-methoxy-5-(2,5-dimethoxyphenyl)-2H-pyrrol-2-ylidene)methyl)-3,5-dimethyl-1H-pyrrole [Compound 19];

2-((5-(benzo[d][1,3]dioxol-5-yl)-3-methoxy-2H-pyrrol-2-ylidene)methyl)-3,5-dimethyl-1H-pyrrole [Compound 20];

2-((5-(4-(2-(pyrrolidin-1-yl)ethoxy)phenyl)-3-methoxy-2H-pyrrol-2-ylidene)methyl)-3,5-dimethyl-1H-pyrrole [Compound 21];

4-(4-methoxy-5-((3,5-dimethyl-1H-pyrrol-2-yl)methylene)-5H-pyrrol-2-yl)-N,N-dimethylbenzenamine [Compound 22];

2-((5-(2,3-dihydrobenzo[b][1,4]dioxin-7-yl)-3-methoxy-2H-pyrrol-2-ylidene)methyl)-3,5-dimethyl-1H-pyrrole [Compound 23];

2-((3-methoxy-5-(4-methoxy-3-methylphenyl)-2H-pyrrol-2-ylidene)methyl)-3,5-dimethyl-1H-pyrrole [Compound 24];

(4-(4-methoxy-5-((3,5-dimethyl-1H-pyrrol-2-yl)methylene)-5H-pyrrol-2-yl)phenyl)(pyrrolidin-1-yl)methanone [Compound 25];

2-((5-(3-fluoro-4-methoxyphenyl)-3-methoxy-2H-pyrrol-2-ylidene)methyl)-3,5-dimethyl-1H-pyrrole [Compound 26];

2-((3-methoxy-5-(2-methoxynaphthalen-6-yl)-2H-pyrrol-2-ylidene)methyl)-3,5-dimethyl-1H-pyrrole [Compound 27];

2-((3-methoxy-5-(3,4,5-trimethoxyphenyl)-2H-pyrrol-2-ylidene)methyl)-3,5-dimethyl-1H-pyrrole. [Compound 28];

2-((5-(4-bromophenyl)-3-methoxy-2H-pyrrol-2-ylidene)methyl)-3,5-dimethyl-1H-pyrrole [Compound 29];

2-methoxy-3-(4-methoxy-5-((3,5-dimethyl-1H-pyrrol-2-yl)methylene)-5H-pyrrol-2-yl)pyridine [Compound 30];

2-((5-(2,3-dihydrobenzofuran-6-yl)-3-methoxy-2H-pyrrol-2-ylidene)methyl)-3,5-dimethyl-1H-pyrrole [Compound 31];

2,4-dimethoxy-5-(4-methoxy-5-((3,5-dimethyl-1H-pyrrol-2-yl)methylene)-5H-pyrrol-2-yl)pyrimidine [Compound 32];

2-chloro-3-(4-methoxy-5-((3,5-dimethyl-1H-pyrrol-2-yl)methylene)-5H-pyrrol-2-yl)pyridine [Compound 33];

3,4-dihydro-7-(4-methoxy-5-((3,5-dimethyl-1H-pyrrol-2-yl)methylene)-5H-pyrrol-2-yl)-4-methyl-2H-benzo[b][1,4]oxazine [Compound 34];

5-(4-methoxy-5-((3,5-dimethyl-1H-pyrrol-2-yl)methylene)-5H-pyrrol-2-yl)pyrimidine [Compound 35];

2-((5-(4-(isopropylthio)phenyl)-3-methoxy-2H-pyrrol-2-ylidene)methyl)-3,5-dimethyl-1H-pyrrole [Compound 36];

1-benzyl-4-(4-methoxy-5-((3,5-dimethyl-1H-pyrrol-2-yl)methylene)-5H-pyrrol-2-yl)-1H-pyrazole [Compound 37];

2-methoxy-5-(4-methoxy-5-((3,5-dimethyl-1H-pyrrol-2-yl)methylene)-5H-pyrrol-2-yl)phenol [Compound 38];

2-fluoro-5-(4-methoxy-5-((3,5-dimethyl-1H-pyrrol-2-yl)methylene)-5H-pyrrol-2-yl)pyridine [Compound 39];

2-fluoro-3-(4-methoxy-5-((3,5-dimethyl-1H-pyrrol-2-yl)methylene)-5H-pyrrol-2-yl)pyridine [Compound 40];

2-((5-(4-(tert-butoxymethyl)phenyl)-3-methoxy-2H-pyrrol-2-ylidene)methyl)-3,5-dimethyl-1H-pyrrole [Compound 41];

2-methoxy-5-(4-methoxy-5-((3,5-dimethyl-1H-pyrrol-2-yl)methylene)-5H-pyrrol-2-yl)pyridine [Compound 42];

3-(benzyloxy)-5-(3,4-dimethoxyphenyl)-2-((3,5-dimethyl-1H-pyrrol-2-yl)methylene)-2H-pyrrole [Compound 43]; or 5-(benzo[d][1,3]dioxol-5-yl)-3-(benzyloxy)-2-((3,5-dimethyl-1H-pyrrol-2-yl)methylene)-2H-pyrrole [Compound 44].

The invention also provides a method for treating cancer or a neoplastic disease in a subject in need of treatment of cancer or a neoplastic disease, wherein the method comprises administering to the subject (i) an effective amount of Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 or a pharmaceutically acceptable salt thereof; and (ii) a pharmaceutically acceptable carrier. The invention also provides a method for treating cancer or a neoplastic disease in a subject in need of treatment of cancer or a neoplastic disease, wherein the method comprises administering to the subject (i) an effective amount of Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 or a pharmaceutically acceptable salt thereof; (ii) a pharmaceutically acceptable carrier; and (iii) a therapeutic agent other than Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44, such as another chemotherapeutic agent. Combinations of Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, and 44 may also be administered to treat the cancer or the neoplastic disease.

The invention provides methods for inhibiting or reducing the growth of a cancer cell or neoplastic cell, wherein the method comprises contacting the cancer cell or the neoplastic cell with an effective amount of Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 or a pharmaceutically acceptable salt thereof.

The invention further provides a method for treating a viral infection in a subject in need of treatment of a viral infection, wherein the method comprises administering to the subject (i) an effective amount of Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 or a pharmaceutically acceptable salt thereof; and (ii) a pharmaceutically acceptable carrier. The invention also provides a method for treating a viral infection in a subject in need of treatment of a viral infection, wherein the method comprises administering to the subject (i) an effective amount of Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 or a pharmaceutically acceptable salt thereof; (ii) a pharmaceutically acceptable carrier; and (iii) a therapeutic agent other than Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44, such as another-antiviral agent. Combinations of Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, and 44 may also be administered to treat viral infections.

The invention also provides methods for inhibiting or reducing the replication or infectivity of a virus, wherein the method comprises contacting a cell infected with the virus with an effective amount of Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 or a pharmaceutically acceptable salt thereof. The invention also provides methods for inhibiting or reducing the propagation of a virus-infected cell, wherein the method comprises contacting the virus-infected cell with an effective amount of Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 or a pharmaceutically acceptable salt thereof.

The invention provides a pharmaceutical composition comprising a pharmaceutically acceptable carrier or vehicle and an effective amount of a Dipyrrole Compound having the Formula (Ia)

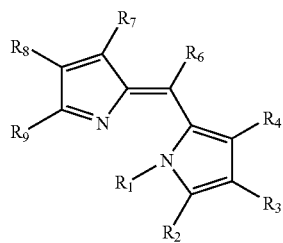

(Ia)

or a pharmaceutically acceptable salt thereof
wherein
$R_1$ is —H, —$C_1$-$C_8$ alkyl or —OH;
$R_2$ is —H, halogen, —$NH_2$, —CN, —$NO_2$, —$N_3$, —COOH, —C(O)$NH_2$, —SH, —S(O)$NH_2$, —S(O)$_2NH_2$, —$C_1$-$C_{10}$ (oxy)alkyl, —$C_1$-$C_{10}$ alkyl, —$C_1$-$C_{10}$ alkoxy, —$C_1$-$C_{10}$ (hydroxy)alkyl, —$C_1$-$C_{10}$ (amino)alkyl, —$C_2$-$C_{10}$ alkenyl, —$C_2$-$C_{10}$ alkynyl, —($C_3$-$C_7$) cycloalkyl, -aryl, —$C_1$-$C_{10}$ (aryl)alkyl, 3- to 12-membered heterocycle, —$OR_{12}$, —$CH_2OR_{10}$, —O($CH_2$)$_n OR_{10}$, —C(O)$R_{10}$, —O—C(O)$R_{10}$, —C(O)($CH_2$), —$R_{10}$, —O—C(O)$OR_{10}$, —O—C(O)$NHR_{10}$, —O—C(O)N($R_{10}$)$_2$, —C(O)N($R_{10}$)$_2$, —C(O)$OR_{10}$, —C(O)$NHR_{10}$, —S—$R_{10}$, —$SOR_{10}$, —S(O)$_2R_{10}$, —S(O)$_2NHR_{10}$, —NHC(O)$R_{10}$, —$NHSR_{10}$, —$NHSOR_{10}$, —NHS(O)$_2R_{10}$, O—C(S)$R_{10}$, O—C(S)$OR_{10}$, O—C(S)$NHR_{10}$, O—C(S)N($R_{10}$)$_2$, —C(S)$OR_{10}$, —C(S)$NHR_{10}$, —C(S)N($R_{10}$)$_2$, —NHC(S)$R_{10}$, —$NR_{10}$C(S)$R_{10}$, —NHC(S)$NHR_{10}$, —NHC(S)N($R_{10}$)$_2$, $NR_{10}$C(S)$NHR_{10}$, —$NR_{10}$C(S)N($R_{10}$)$_2$ or $R_2$ and $R_3$, together with the carbon atom to which each is attached, join to form a 5- to 9-membered ring;
$R_3$ and $R_4$ are independently —H, halogen, —$NH_2$, —CN, —$NO_2$, —$N_3$, —COOH, —C(O)$NH_2$, —SH, —S(O)$NH_2$, —S(O)$_2NH_2$, —$C_1$-$C_{10}$ (oxy)alkyl, —$C_1$-$C_{10}$ alkyl, —$C_1$-$C_{10}$ alkoxy, —$C_1$-$C_{10}$ (hydroxy)alkyl, —$C_1$-$C_{10}$ (amino)alkyl, —$C_2$-$C_{10}$ alkenyl, —$C_2$-$C_{10}$ alkynyl, —($C_3$-$C_7$)cycloalkyl, -aryl, —$C_1$-$C_{10}$ (aryl)alkyl, 3- to 12-membered heterocycle, —$OR_{10}$—$CH_2OR_{10}$, —O($CH_2$)$_n OR_{10}$, —C(O)$R_{10}$, —O—C(O)$R_{10}$, —C(O)($CH_2$), —$R_{10}$, —O—C(O)$OR_{10}$, —O—C(O)$NHR_{10}$, —O—C(O)N($R_{10}$)$_2$, —C(O)N($R_{10}$)$_2$, —C(O)$OR_{10}$, —C(O)$NHR_{10}$, —S—$R_{10}$, —$SOR_{10}$, —S(O)$_2R_{10}$, —S(O)$_2NHR_{10}$, —NHC(O)$R_{10}$, —$NHSR_{10}$—$NHSOR_{10}$, —NHS(O)$_2R_{10}$, O—C(S)$R_{10}$, O—C(S)$OR_{10}$; O—C(S)$NHR_{10}$, O—C(S)N($R_{10}$)$_2$, —C(S)$OR_{10}$, —C(S)$NHR_{10}$, —C(S)N($R_{10}$)$_2$, —NHC(S)$R_{10}$, —$NR_{10}$C(S)$R_{10}$, —NHC(S)$NHR_{10}$, —NHC(S)N($R_{10}$)$_2$, —$NR_{10}$C(S)$NHR_{10}$, —$NR_{10}$C(S)N($R_{10}$)$_2$ or $R_2$ and $R_3$, or $R_3$ and $R_4$, together with the carbon atom to which each is attached, join to form a 5- to 9-membered ring;
$R_6$ is —H, halogen, —OH, —$NH_2$, —$C_1$-$C_8$ alkyl, or —O—($C_1$-$C_8$ alkyl);
$R_7$ and $R_8$ are independently —H, —OH, halogen, amino, —NH($C_1$-$C_5$ alkyl), —N($C_1$-$C_5$ alkyl)$_2$, —NH(phenyl), —N(phenyl)$_2$, —NH(naphthyl), —N(naphthyl)$_2$, —CN, —$NO_2$, —$N_3$, —$C_1$-$C_8$ alkyl, —O—($C_1$-$C_8$ alkyl), —($C_1$-$C_8$ alkyl)-OH, —O-benzyl, —$C_2$-$C_8$ alkenyl, —$C_2$-$C_8$ alkynyl, —$C_3$-$C_{12}$ cycloalkyl, -phenyl, -naphthyl, -3- to 12-membered heterocycle, —$OR_{10}$, —$CH_2OR_{10}$, —O($CH_2$)$_n R_{10}$, —O($CH_2$)$_n OR_{10}$, —$CH_2$—O—($CH_2$)$_n OR_{10}$, —O—C(O)$R_{10}$, —C(O)($CH_2$)$_n$—$R_{10}$, —C(O)$R_{10}$, —O—C(O)$OR_{10}$, —O—C(O)$NHR_{10}$, —O—C(O)N($R_{10}$)$_2$, —C(O)N($R_{10}$)$_2$, —C(O)$OR_{10}$, —C(O)$NHR_{10}$, —S—$R_{10}$, —$SOR_{10}$, —S(O)$_2R_{10}$, —NHC(O)$R_{10}$, —$NHSR_{10}$, —$NHSOR_{10}$, —NHS(O)$_2R_{10}$, O—C(S)$R_{10}$, O—C(S)$OR_{10}$, O—C(S)$NHR_{10}$, O—C(S)N($R_{10}$)$_2$, —C(S)$OR_{10}$, —C(S)$NHR_{10}$, —C(S)N($R_{10}$)$_2$, —NHC(S)$R_{10}$, —$NR_{10}$C(S)$R_{14}$, —NHC(S)$NHR_{10}$, —NHC(S)N($R_{10}$)$_2$, —$NR_{10}$C(S)$NHR_{10}$, —$NR_{10}$C(S)N($R_{10}$)$_2$;
$R_9$ is —($C_1$-$C_{10}$) alkyl, —($C_3$-$C_{12}$) cycloalkyl, -aryl, —$C_1$-$C_{10}$ (aryl)alkyl, 3- to 12-membered heterocycle;
with the proviso that $R_2$, $R_3$, $R_4$, $R_7$, $R_5$ or $R_9$ is not pyrrole or indole;
each $R_{10}$ is independently —H, —$C_1$-$C_8$ alkyl, —$C_3$-$C_{12}$ cycloalkyl, -aryl, -3- to 12-membered heterocycle, —$C_2$-$C_8$ alkenyl, or —$C_2$-$C_8$ alkynyl;
$R_{12}$ is —$C_1$-$C_8$ alkyl, —$C_3$-$C_{12}$ cycloalkyl, -aryl, -3- to 12-membered heterocycle, —$C_2$-$C_8$ alkenyl, or —$C_2$-$C_8$ alkynyl;
each n is independently an integer ranging from 0 to 6; and
wherein
when $R_2$ is ethyl, $R_4$ is other than —H, or
when $R_9$ is ethyl, $R_7$ is other than —H.

In certain embodiments, $BF_3$ adducts are not salts within the scope of the invention.

In certain embodiments, $R_1$ and the pyrrole ring N atoms in Formula Ia do not form a third ring structure.

In certain embodiments, when $R_2$ in Formula Ia is $C_{1-10}$ alkyl then $R_4$ in Formula Ia is other than —H. In certain embodiments, when $R_9$ in Formula Ia is $C_{1-10}$ alkyl then $R_7$ in Formula Ia is other than —H.

In certain embodiments, each n in Formula Ia is an integer from 1 to 6.

In certain embodiments, $R_9$ in Formula Ia is selected from the group consisting of aryl and a 3- to 12-membered heterocycle with the proviso that $R_9$ is not pyrrole or indole.

In certain embodiments, $R_7$ in Formula Ia is —O—($C_1$-$C_8$ alkyl).

In certain embodiments, $R_7$ in Formula Ia is —$OCH_3$.

In certain embodiments, $R_2$ and $R_4$ in Formula Ia are independently $C_1$-$C_{10}$ alkyl.

In certain embodiments, $R_2$ and $R_4$ in Formula Ia are both —$CH_3$.

In certain embodiments, $R_3$ in Formula Ia is —H.
In certain embodiments, $R_3$ in Formula Ia is —H.
In certain embodiments, $R_8$ in Formula Ia is —H.
In certain embodiments, $R_1$ in Formula Ia is —H.
In certain embodiments, $R_7$ in Formula Ia is —O—($C_1$-$C_8$ alkyl) substituted with phenyl.

In certain embodiments, $R_7$ in Formula Ia is —O-benzyl.
In certain embodiments, $R_7$ in Formula Ia is unsubstituted —O-benzyl.

The invention provides a pharmaceutical composition comprising a pharmaceutically acceptable carrier or vehicle and an effective amount of a Dipyrrole Compound having the Formula (Ib)

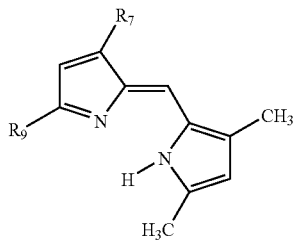

wherein
$R_9$ is —($C_3$-$C_{12}$) cycloalkyl, -aryl, —$C_1$-$C_{10}$ (aryl)alkyl, -3- to 12-membered heterocycle, with the proviso that $R_9$ is not pyrrole or indole; and
$R_7$ is —O—($C_1$-$C_8$ alkyl) or —$OR_{11}$, wherein $R_{11}$ is aryl.

In certain embodiments, $R_9$ in Formula (Ib) is aryl or a 3- to 12-membered heterocycle, with the proviso that $R_9$ is not pyrrole or indole.

In certain embodiments, $R_9$ in Formula (Ib) is selected from the group consisting of substituted and unsubstituted phenyl, quinolinyl, thiophenyl, benzothiophenyl, furyl, napthyl, pyridinyl, dihydrobenzofuranyl, pyrimidinyl, dihydrooxazinylphenyl, and pyrazolyl.

The invention provides a pharmaceutical composition comprising a pharmaceutically acceptable carrier or vehicle and an effective amount of a compound selected from the group consisting of Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44.

In certain embodiments, a pharmaceutical composition of the invention comprises one or more additional therapeutic agents, such as a chemotherapeutic agent. In a more specific aspect, the additional therapeutic agent and the Dipyrrole Compound act synergistically.

The invention further provides a Dipyrrole Compound of the Formula (Ib)

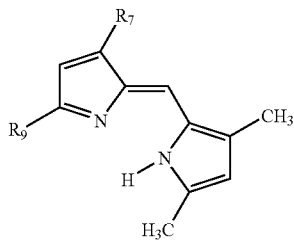

or a pharmaceutically acceptable salt thereof,
wherein
$R_9$ is —($C_3$-$C_{12}$) cycloalkyl, -aryl, —$C_1$-$C_{10}$ (aryl)alkyl, -3- to 12-membered heterocycle, with the proviso that $R_9$ is not pyrrole or indole; and
$R_7$ is —O—($C_1$-$C_8$ alkyl) or —$OR_{11}$, wherein $R_{11}$ is aryl.
In certain embodiments of the Dipyrrole Compounds of the invention, $R_9$ in Formula (Ib) is aryl or a 3- to 12-membered heterocycle, with the proviso that $R_9$ is not pyrrole or indole.

In certain embodiments of the Dipyrrole Compounds of the invention, $R_9$ in Formula (Ib) is aryl selected from substituted and unsubstituted phenyl, anthryl, fluorenyl, indenyl, azulenyl, phenanthryl and naphthyl.

In certain embodiments of the Dipyrrole Compounds of the invention, $R_9$ in Formula (Ib) is a 3- to 12-membered heterocycle selected from the group consisting of substituted and unsubstituted aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, oxazinyl, thiazinyl, diazinyl, triazinyl, tetrazinyl, imidazolyl, benzimidazolyl, tetrazolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzothiazolyl, thiophenyl, pyrazolyl, triazolyl, benzodiazolyl, benzotriazolyl, pyrimidinyl, isoindolyl, indazolyl, benzothiophene, benzodioxole, dibenzofuran and dibenzothiophene.

In certain embodiments of the Dipyrrole Compounds of the invention, $R_9$ in Formula (Ib) is selected from the group consisting of substituted and unsubstituted phenyl, quinolinyl, thienyl, benzothiophenyl, furyl, napthyl, pyridinyl, dihydrobenzofuranyl, pyrimidinyl, dihydrooxazinylphenyl, and pyrazolyl.

In certain embodiments of the Dipyrrole Compounds of the invention, $R_7$ in Formula (Ib) is —$OCH_3$.

In certain embodiments of the Dipyrrole Compounds of the invention, $R_7$ is —O—($C_1$-$C_8$ alkyl).

In certain embodiments of the Dipyrrole Compounds of the invention, $R_7$ is —$OCH_3$.

In certain embodiments of the Dipyrrole Compounds of the invention, $R_7$ is —O—($C_1$-$C_8$ alkyl) substituted with phenyl.

In certain embodiments of the Dipyrrole Compounds of the invention, $R_7$ is —O-benzyl.

In certain embodiments of the Dipyrrole Compounds of the invention, $R_7$ is unsubstituted —O-benzyl.

In certain, more specific embodiments, the invention provides a Dipyrrole Compound selected from the group consisting of: Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44.

3.1 DEFINITIONS AND ABBREVIATIONS

As used herein, "halogen" refers to —F, —Cl, —Br or —I.

As used herein, the term "$C_1$-$C_{10}$ alkyl" means a saturated straight chain or branched non-cyclic hydrocarbon having from 1 to 10 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, -2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like.

As used herein, "$C_1$-$C_8$ alkyl" refers to a straight or branched chain saturated hydrocarbon group containing 1-8 carbon atoms which can be unsubstituted or optionally substituted with one or more -halogen, —NH$_2$, —OH, —O—(C$_1$-C$_8$ alkyl), phenyl or naphthyl groups. Examples of C$_1$-C$_8$ straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, 1-heptyl and 1-octyl.

As used herein, "C$_1$-C$_5$ alkyl" refers to a straight or branched chain saturated hydrocarbon group containing 1-5 carbon atoms. Examples of C$_1$-C$_5$ straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl and 1-pentyl.

As used herein, the term "C$_1$-C$_{10}$ alkoxy" means —O—(C$_1$-C$_{10}$ alkyl), wherein C$_1$-C$_{10}$ alkyl is defined above.

As used herein, the term "aryl" means a carbocyclic aromatic group. All of the ring atoms of an aryl group are carbon atoms. Aryl groups include compounds having one or more ring structures such as mono-, bi-, or tricyclic compounds as well as benzo-fused carbocyclic moieties such as 5,6,7,8-tetrahydronaphthyl and the like. In one embodiment, the aryl group is a monocyclic ring or bicyclic ring. Representative aryl groups include phenyl, tolyl, anthryl, fluorenyl, indenyl, azulenyl, phenanthryl and naphthyl. A carbocyclic aryl group can be unsubstituted or substituted.

As used herein, the term "C$_1$-C$_{10}$ (hydroxy)alkyl" means C$_1$-C$_{10}$ alkyl, wherein C$_1$-C$_{10}$ alkyl is defined above, substituted with one or more —OH groups. Examples of C$_1$-C$_{10}$ (hydroxy)alkyl include, but are not limited to, hydroxymethyl, 1-hydroxyethyl, 2-hydroxyethyl, 1-hydroxypropyl, 2-hydroxypropyl, 3-hydroxypropyl, 4-hydroxybutyl, 5-hydroxypentyl and the like.

As used herein, the term "C$_1$-C$_{10}$ (amino)alkyl" means C$_1$-C$_{10}$ alkyl, wherein C$_1$-C$_{10}$ alkyl is defined above, substituted with one or more —NH$_2$ groups. Examples of C$_1$-C$_{10}$ (amino)alkyl include, but are not limited to, —CH$_2$—NH$_2$, —(CH$_2$)$_2$—NH$_2$, —(CH$_2$)$_3$—NH$_2$, —(CH$_2$)$_4$—NH$_2$, —(CH$_2$)$_5$—NH$_2$ and the like.

As used herein, the term "C$_1$-C$_{10}$ (halo)alkyl" means C$_1$-C$_{10}$ alkyl, wherein C$_1$-C$_{10}$ alkyl is defined above, substituted with one or more —F, —Cl, —Br or —I groups. Examples of C$_1$-C$_{10}$ (halo)alkyl include, but are not limited to, trichloromethyl, trifluoromethyl, dichloromethyl, difluoromethyl, 1-fluoroethyl, 2-chloroethyl, 1-bromopropyl, 2-iodopropyl, 3-chloropropyl, 4-fluorobutyl, 5-chloropentyl and the like.

As used herein, the term "C$_2$-C$_{10}$ alkenyl" means a straight chain or branched non-cyclic hydrocarbon having from 2 to 10 carbon atoms and including at least one carbon-carbon double bond. Representative straight chain and branched C$_2$-C$_{10}$ alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. In one embodiment, C$_2$-C$_6$ alkenyl is a subclass of C$_2$-C$_{10}$ alkenyl. The double bond of a C$_2$-C$_{10}$ alkenyl can be unconjugated or conjugated to another unsaturated group. A —C$_2$-C$_{10}$ alkenyl can be unsubstituted or substituted with, e.g., -amino, —C$_1$-C$_{10}$ (oxy)alkyl, -halogen, —COOH, —C(O)C$_1$-C$_9$ alkyl, —SH, =S, —OH, and —C$_1$-C$_{10}$ alkoxy.

As used herein, "C$_2$-C$_8$ alkenyl" refers to an unsaturated, straight or branched chain hydrocarbon group containing 2-8 carbon atoms and at least one double bond which can be unsubstituted or optionally substituted with a phenyl or naphthyl group.

As used herein, "C$_2$-C$_8$ alkynyl" refers to an unsaturated, straight or branched chain hydrocarbon group containing 2-8 carbon atoms and at least one triple bond which can be unsubstituted or optionally substituted with a phenyl or naphthyl group.

As used herein, unless otherwise specified the term "C$_2$-C$_{10}$ alkynyl" means a straight chain or branched non-cyclic hydrocarbon having from 2-10 carbon atoms and including at lease one carbon-carbon triple bond. Representative straight chain and branched C$_2$-C$_{10}$ alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. In one embodiment, C$_2$-C$_6$ alkynyl is a subclass of C$_2$-C$_{10}$ alkynyl. The triple bond of a C$_2$-C$_{10}$ alkynyl can be unconjugated or conjugated to another unsaturated group. A C$_2$-C$_{10}$ alkynyl can be unsubstituted or substituted with, e.g., -amino, —COOH, -halogen, C$_1$-C$_{10}$ (oxy)alkyl, —C(O)C$_1$-C$_9$ alkyl, —SH, =S, —OH, C$_1$-C$_{10}$ alkoxy, and C$_1$-C$_{10}$ alkyl.

As used herein, the term "(C$_3$-C$_7$) cycloalkyl" means a monocyclic or bicyclic saturated ring consisting of carbon and hydrogen atoms and having 3-7 carbon atoms. A (C$_3$-C$_7$) cycloalkyl can be unsubstituted or substituted with, e.g., -amino, —COOH, -halogen, C$_1$-C$_{10}$ (oxy)alkyl, —C(O)C$_1$-C$_9$ alkyl, —SH, =S, —OH, C$_1$-C$_{10}$ alkoxy, and C$_1$-C$_{10}$ alkyl. Examples of (C$_3$-C$_7$) cycloalkyl include, but are not limited to, cyclopropyl, cyclobutyl, cyclopentyl, cyclohexyl, and cycloheptyl, and saturated cyclic and bicyclic terpenes.

As used herein, "C$_3$-C$_{12}$ cycloalkyl" refers to a non-aromatic, saturated monocyclic, bicyclic or tricyclic hydrocarbon ring system containing 3-12 carbon atoms. Examples of C$_3$-C$_{12}$ cycloalkyl groups include but are not limited to cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

As used herein, a "-3- to 12-membered heterocycle" is a 3- to 12-membered aromatic or nonaromatic monocyclic, bicyclic or tricyclic ring of carbon atoms and from 1 to 4 heteroatoms selected from oxygen, nitrogen and sulfur. Examples of 3- to 12-membered heterocycles include, but are not limited to, aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzothiazolyl, thiophenyl, pyrazolyl, triazolyl, benzodiazolyl, benzotriazolyl, pyrimidinyl, isoindolyl, indazolyl, benzothiophene and benzodioxole, dibenzofuran and dibenzothiophene.

As used herein, an —O-benzyl group can be substituted or unsubstituted.

As used herein, the term "—C$_1$-C$_{10}$ (oxy)alkyl" refers to a C$_1$-C$_{10}$ alkyl group, as defined herein, having one or more carbonyl (i.e., ketone or aldehyde) groups. Examples of —$C_1$-$C_{10}$(oxy)alkyl groups include, but are not limited to, formyl, acyl, propionaldehyde, butyraldehyde, isobutyraldehyde and pivalaldehyde.

As used herein, the term "—$C_1$-$C_{10}$(aryl)alkyl" refers an aryl group that is attached to another group by a ($C_1$-$C_{10}$) alkylene group. Representative arylalkyl groups include benzyl, 2-phenyl-ethyl, naphth-3-yl-methyl and the like.

As used herein, a -phenyl group can be substituted or unsubstituted.

When the groups described herein are said to be "substituted or unsubstituted," when substituted, they may be substituted with any desired substituent or substituents that do not adversely affect the desired activity of the compound. Examples of preferred substituents are those found in the exemplary compounds and embodiments disclosed herein, as well as halogen (chloro, iodo, bromo, or fluoro); $C_{1-6}$ alkyl; $C_{2-6}$ alkenyl; $C_{2-6}$ alkynyl; hydroxyl; $C_{1-4}$ alkoxyl; amino; nitro; thiol; thioether; imine; cyano; amido; phosphonato; phosphine; carboxyl; thiocarbonyl; sulfonyl; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); benzyloxy; amino (primary, secondary, or tertiary); —$N(CH_3)_2$; O-lower alkyl; O-aryl, aryl; aryl-lower alkyl; $CO_2CH_3$; —$OCH_2CH_3$; methoxy; $CONH_2$; $OCH_2CONH_2$; $NH_2$; $SO_2NH_2$; $OCHF_2$; $CF_3$; $OCF_3$; and such moieties may also be optionally substituted by a fused-ring structure or bridge, for example —$OCH_2O$—, —$O(CH_2)_2O$—, —$O(CH_2)_3O$—, and the like.

These substituents may optionally be further substituted with a substituent selected from such groups.

An "effective amount" in the context of a viral infection is an amount of a Dipyrrole Compound that is sufficient to reduce or ameliorate the severity and/or duration of the viral infection, or one or more symptoms thereof, prevent the advancement of the viral infection, prevent the recurrence, development, or onset of one or more symptoms associated with the viral infection, prevent or reduce the replication or multiplication of a virus, prevent or reduce the production and/or release of a viral particle, enhance or improve the prophylactic or therapeutic effect(s) of another therapy. In certain aspects, an "effective amount" of a Dipyrrole Compound in the context of a viral infection is an amount sufficient to reduce one or more of the following steps of a life cycle of a virus: the docking of the virus particle to a cell, the introduction of viral genetic information into a cell, the expression of viral proteins, the production of new virus particles and the release of virus particles from a cell by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. In another specific embodiment, an effective amount of a Dipyrrole Compound in the context of a viral infection reduces the replication, multiplication or spread of a virus by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

An "effective amount" in the context of cancer or a neoplastic disease is an amount of a Dipyrrole Compound that is sufficient to reduce or ameliorate the severity and/or duration of the cancer or neoplastic disease, or one or more symptoms thereof, prevent the advancement of the cancer or neoplastic disease, prevent the recurrence, development, or onset of one or more symptoms associated with the cancer or neoplastic disease, prevent or reduce the propagation of a cancer cell or neoplastic cell, enhance or improve the prophylactic or therapeutic effect(s) of another anti-cancer or anti-neoplastic disease therapy. In certain aspects, an "effective amount" of a Dipyrrole Compound in the context of a cancer or neoplastic disease is an amount sufficient to reduce the propagation of a cancer cell or a neoplastic cell by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

An "effective amount" in the context of inhibiting the growth of a cancer cell or a neoplastic cell is an amount of a Dipyrrole Compound that is sufficient to reduce the propagation of a cancer cell or a neoplastic cell by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%.

The phrase "substantially anhydrous," as used herein in connection with a reaction mixture or an organic solvent, means that the reaction mixture or organic solvent comprises less than about 1 percent of water by weight; in one embodiment, less than about 0.5 percent of water by weight; and in another embodiment, less than about 0.25 percent of water by weight of the reaction mixture or organic solvent.

In one embodiment, when administered to a patient, e.g., a mammal for veterinary use or a human for clinical use, the Dipyrrole Compounds are administered in isolated form. As used herein, "isolated" means that the Dipyrrole Compounds are separated from other components of either (a) a natural source, such as a plant or cell, preferably bacterial culture, or (b) a synthetic organic chemical reaction mixture. In another embodiment, via conventional techniques, the Dipyrrole Compounds are purified. As used herein, "purified" means that when isolated, the isolate contains at least 95%, preferably at least 98%, of a single Dipyrrole Compound by weight of the isolate.

As used herein, the term "T/C value" refers to the value obtained when: (a) the change from baseline in average tumor volume of treated mice is divided by the change from baseline in the average tumor volume of negative control mice; and (b) the numerical value obtained in step (a) is multiplied by 100.

It is recognized that Dipyrrole Compounds of the invention can have one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention or the compounds to be used with the methods of the invention, encompass all of the corresponding enantiomers and stereoisomers, that is, both the stereomerically pure form (e.g., geometrically pure, enantiomerically pure, or diastereomerically pure) and enantiomeric and stereoisomeric mixtures, e.g., racemates.

Similarly, where Dipyrrole Compounds differ only by the placement of a proton and the corresponding location of a double-bond (tautomerism), the chemical structures depicted herein, and therefore the compounds of the invention or the compounds to be used with the methods of the invention, encompass all of the corresponding tautomers and the mixture of the tautomers.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diasteroemers of the compound. A typical stereomerically pure compound comprises greater than about 80% by weight of stereoisomer of the compound and less than about 20% by weight of other stereoisomers the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

Enantiomeric and stereoisomeric mixtures of compounds of the invention can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

The following abbreviations and their definitions, unless defined otherwise, are used in this specification:

| Abbreviation | Definition |
| --- | --- |
| BOC | —C(O)OC(CH$_3$)$_3$ |
| DEF | N,N-diethylformamide |
| dppf | 1,1-bis(diphenylphosphino)ferrocene |
| DMF | N,N-dimethylformamide |
| DMSO | dimethylsulfoxide |
| THF | tetrahydrofuran |
| EtOAc | ethyl acetate |
| EtOH | ethanol |
| MeOH | methanol |
| Tf | —SO$_2$CF$_3$ |
| dba | dibenzylideneacetone |
| Ph | Phenyl |
| TBDMSCl | tert-Butyldimethylsilyl chloride |
| DBU | 1,8-diazabicyclo[5.4.0]undec-7-ene |
| LC/MS | Liquid Chromatography/Mass Spectrometry |

4. BRIEF DESCRIPTION OF THE DRAWINGS

5. DETAILED DESCRIPTION OF THE INVENTION

Figure 1:
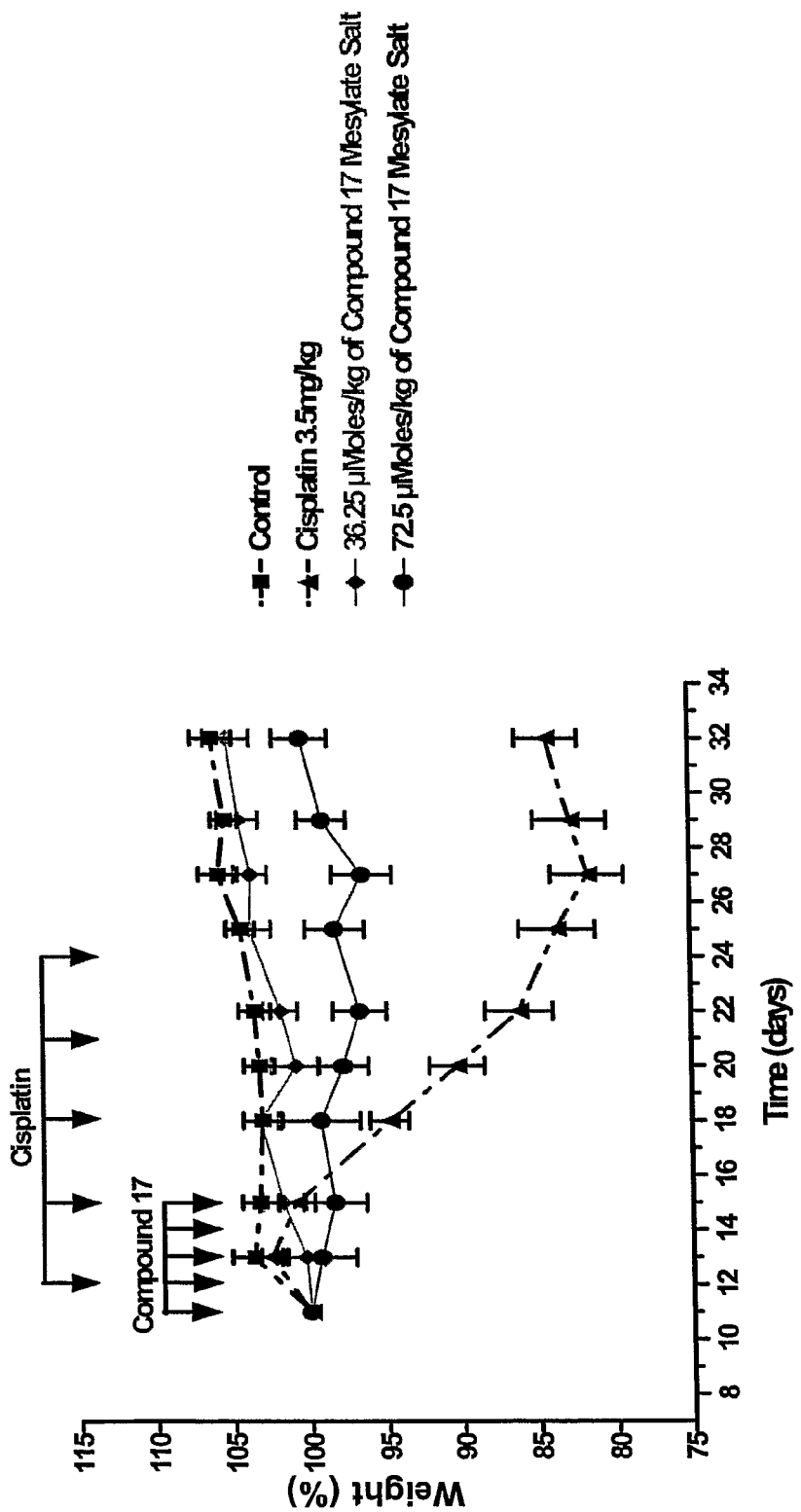
FIG. 1 illustrates the variation in body weight of SCID mice over time following treatment with cisplatin at a dose of 3.5 mg/kg or Compound 17 mesylate salt (MS) at a dose of 36.25 μMoles/kg or 72.5 μMoles/kg.

5.1 The Dipyrrole Compounds of Formula (Ia)

In certain embodiments, Dipyrrole Compounds have Formula (Ia)

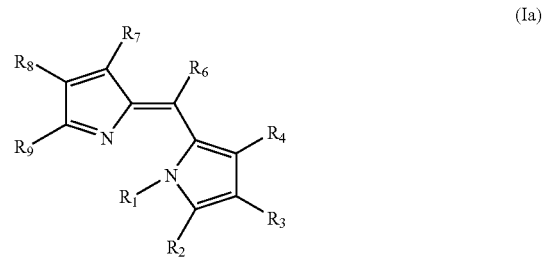

(Ia)

or are pharmaceutically acceptable salts thereof, wherein: $R_1$-$R_4$, and $R_6$-$R_9$ are defined above for the compounds of formula (Ia) for use with the methods of the invention.

A first subclass of the Dipyrrole Compounds of Formula (Ia) is that wherein: n is an integer from 1 to 6.

A second subclass of the Dipyrrole Compounds of Formula (Ia) is that wherein: $R_9$ in Formula (Ia) is selected from the group consisting of aryl and a 3- to 12-membered heterocycle with the proviso that $R_9$ is not pyrrole or indole.

A third subclass of the Dipyrrole Compounds of Formula (Ia) is that wherein: $R_7$ in Formula (Ia) is —O—($C_1$-$C_8$ alkyl).

A fourth subclass of the Dipyrrole Compounds of Formula (Ia) is that wherein: $R_7$ in Formula (Ia) is —OCH$_3$.

A fifth subclass of the Dipyrrole Compounds of Formula (Ia) is that wherein: $R_7$ in Formula (Ia) is —O—($C_1$-$C_8$ alkyl) optionally substituted by phenyl.

A sixth subclass of the Dipyrrole Compounds of Formula (Ia) is that wherein: $R_7$ in Formula (Ia) is —O-benzyl.

A seventh subclass of the Dipyrrole Compounds of Formula (Ia) is that wherein: the —O-benzyl in Formula (Ia) is unsubstituted.

A eighth subclass of the Dipyrrole Compounds of Formula (Ia) is that wherein: $R_2$ and $R_4$ in Formula (Ia) are independently $C_1$-$C_{10}$ alkyl.

A ninth subclass of the Dipyrrole Compounds of Formula (Ia) is that wherein: $R_2$ and $R_4$ in Formula (Ia) are both —CH$_3$.

A tenth subclass of the Dipyrrole Compounds of Formula (Ia) is that wherein: (i) $R_3$ in Formula (Ia) is —H and (ii) $R_2$ and $R_4$ in Formula (Ia) are both —CH$_3$.

A eleventh subclass of the Dipyrrole Compounds of Formula (Ia) is that wherein: $R_3$ in Formula (Ia) is —H.

A twelfth subclass of the Dipyrrole Compounds of Formula (Ia) is that wherein: $R_9$ in Formula (Ia) is —H.

A thirteenth subclass of the Dipyrrole Compounds of Formula (Ia) is that wherein: $R_1$ in Formula (Ia) is —H.

A fourteenth subclass of the Dipyrrole Compounds of Formula (Ia) is that wherein: $R_9$ in Formula (Ia) is aryl selected from substituted and unsubstituted phenyl, anthryl, fluorenyl, indenyl, azulenyl, phenanthryl and naphthyl.

A fifteenth subclass of the Dipyrrole Compounds of Formula (Ia) is that wherein: $R_9$ is a 3- to 12-membered heterocycle selected from the group consisting of substituted and unsubstituted aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, oxazinyl, thiazinyl, diazinyl, triazinyl, tetrazinyl, imidazolyl, benzimidazolyl, tetrazolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzothiazolyl, thiophenyl, pyrazolyl, triazolyl, benzodiazolyl, benzotriazolyl, pyrimidinyl, isoindolyl, indazolyl, benzothiophene, benzodioxole, dibenzofuran and dibenzothiophene.

A sixteenth subclass of the Dipyrrole Compounds of Formula (Ia) is that wherein: when $R_2$ in Formula Ia is $C_{1-10}$ alkyl then $R_4$ in Formula Ia is other than —H.

A seventeenth subclass of the Dipyrrole Compounds of Formula (Ia) is that wherein: $R_9$ in Formula Ia is $C_{1-10}$ alkyl then $R_7$ in Formula Ia is other than —H.

In certain embodiments, $BF_3$ adducts are not salts of Dipyrrole Compounds.

In certain embodiments, $R_1$ and the pyrrole ring N atoms in Formula Ia do not form a third ring structure.

In certain embodiments, one or more of $R_2$, $R_3$, $R_4$, $R_7$, $R_8$, $R_9$ is a 3- to 12-membered heterocycle. In more specific embodiments, one or more of $R_2$, $R_3$, $R_4$, $R_7$, $R_8$, $R_9$ is a bicycle, a 6-membered heterocycle, a sulfur-containing heterocycle, an oxygen-containing heterocycle, a heterocycle with one heteroatom, a heterocycle with two heteroatoms, or a heterocycle with three heteroatoms.

5.2 The Dipyrrole Compounds of Formula (Ib)

The present invention provides Dipyrrole Compounds having the Formula (Ib)

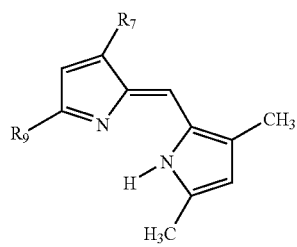

Ib wherein $R_9$ is —$(C_3$-$C_{12})$ cycloalkyl, -aryl, —$C_1$-$C_{10}$ (aryl)alkyl, -3- to 12-membered heterocycle, with the proviso that $R_9$ is not pyrrole or indole; and $R_7$ is —O—$(C_1$-$C_8$ alkyl) or —$OR_{11}$, wherein $R_{11}$ is aryl.

In a first subclass of the Dipyrrole Compounds of Formula (Ib), $R_9$ is aryl or a 3- to 12-membered heterocycle, with the proviso that $R_9$ is not pyrrole or indole.

In a second subclass of the Dipyrrole Compounds of Formula (Ib), $R_9$ is selected from the group consisting of substituted and unsubstituted phenyl, quinolinyl, thienyl, benzothiophenyl, furyl, napthyl, pyridinyl, dihydrobenzofuranyl, pyrimidinyl, dihydrooxazinylphenyl, and pyrazolyl.

In a third subclass, $R_7$ is methoxy.

In certain embodiments, $R_9$ is a 3- to 12-membered heterocycle. In more specific embodiments, $R_9$ is a bicycle, a 6-membered heterocycle, a sulfur-containing heterocycle, an oxygen-containing heterocycle, a heterocycle with one heteroatom, a heterocycle with two heteroatoms, Or a heterocycle with three heteroatoms.

5.3 Illustrative Dipyrrole Compounds

The invention provides the following illustrative Dipyrrole Compounds, Compound 1 to Compound 44:

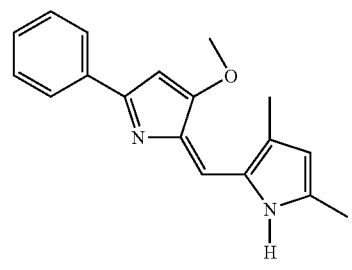

1

3-methoxy-2-((3,5-dimethyl-1H-pyrrol-2-yl)methylene)-5-phenyl-2H-pyrrole

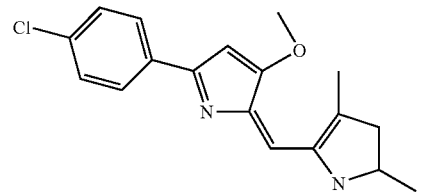

2

2-((5-4-chlorophenyl)-3-methoxy-2H-pyrrol-2-ylidene)methyl)-3,5-dimethyl-1H-pyrrole

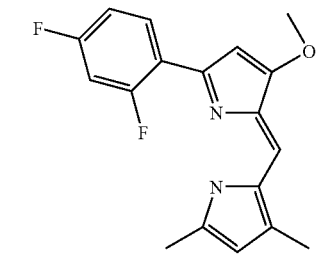

3

5-(2,4-difluorophenyl)-3-methoxy-2-((3,5-dimethyl-1H-pyrrol-2-yl)methylene)-2H-pyrrole

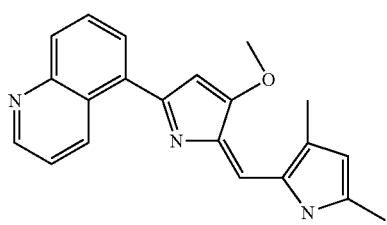

5-(4-methoxy-5-((3,5-dimethyl-1H-pyrrol-2-yl)methylene)-5H-pyrrol-2-yl)quinoline

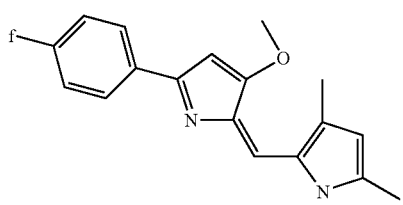

2-((5-4-fluorophenyl)-3-methoxy-2H-pyrrol-2-ylidene)methyl)-3,5-dimethyl-1H-pyrrole

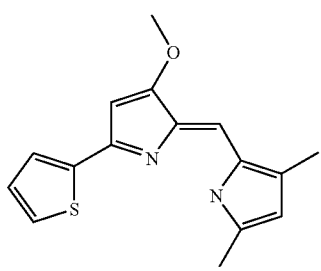

3-methoxy-2-((3,5-dimethyl-1H-pyrrol-2-yl)methylene)-5-(thiophen-2-yl)-2H-pyrrole

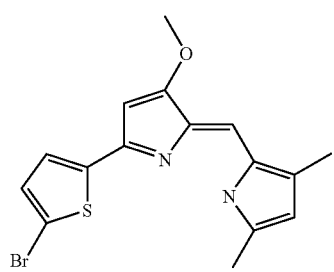

5-(5-bromothiophen-2-yl)-3-methoxy-2-((3,5-dimethyl-1H-pyrrol-2-yl)methylene)-2H-pyrrole

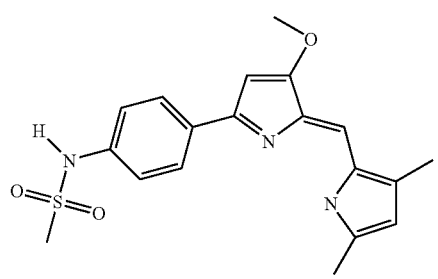

N-4-(4-methoxy-5-((3,5-dimethyl-1H-pyrrol-2-yl)methylene)-5H-pyrrol-2-yl)-phenyl-methylsulfonamide

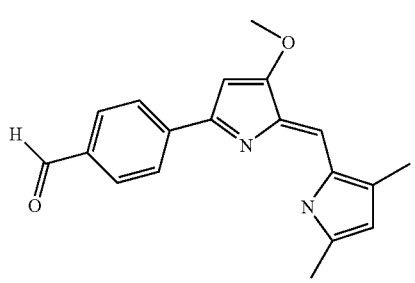

4-(4-methoxy-5-((3,5-dimethyl-1H-pyrrol-2-yl)methylene)-5H-pyrrol-2-yl)-benzaldehyde

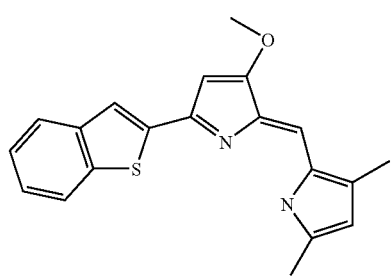

5(benezo[b]thiophen-2-yl)-3-methoxy-2-((3,5-dimethyl-1H-pyrrol-2-yl)methylene)-2H-pyrrole

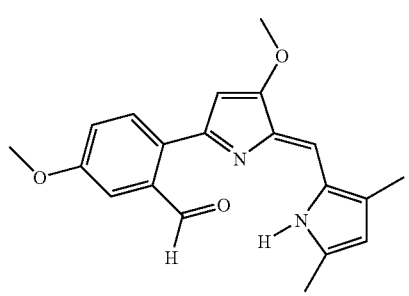

5-methoxy-2-(4-methoxy-5-((3,5-dimethyl-1H-pyrrol-2-yl)methylene)-5H-pyrrol-2-yl)benzaldehyde

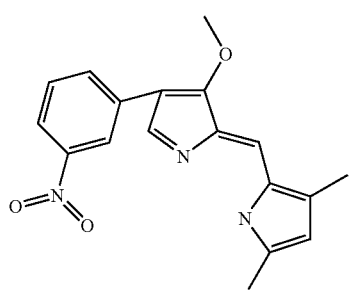

3-methoxy-2-((3,5-dimethyl-1H-pyrrol-2-yl)methylene)-5-(3-nitrophenyl)-2H-pyrrole

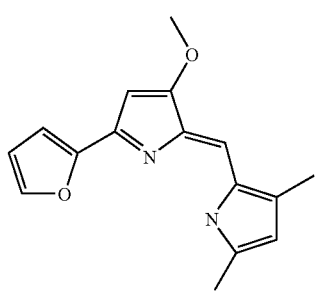

2-((5-(furan-2-yl)-3-methoxy-2H-pyrrol-2-
ylidene)methyl)-3,5-dimethyl-1H-pyrrole

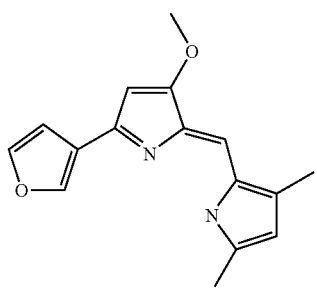

2-((5-(furan-3-yl)-3-methoxy-2H-pyrrol-2-
ylidene)methyl)-3,5-dimethyl-1H-pyrrole

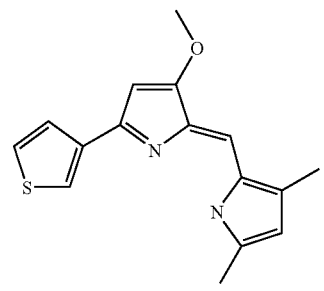

2-((3-methoxy-5-(thiophen-3-yl)-2H-pyrrol-
2-ylidene)methyl)-3,5dimethyl-1H-pyrrole

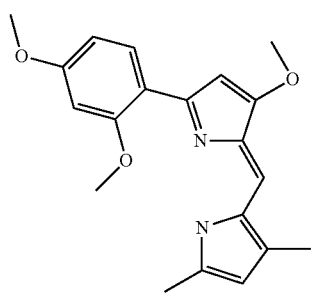

3-methoxy-5-(2,4-dimethoxyphenyl)-2-
((3,5-dimethyl-1H-pyrrol-2-yl)methylene)-
2H-pyrrole

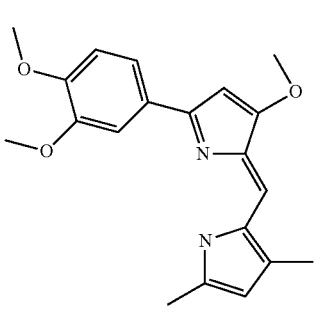

3-methoxy-5-(3,4-dimethoxyphenyl)-2-((3,5-
dimethyl-1H-pyrrol-2-yl)methylene)-2H-
pyrrole

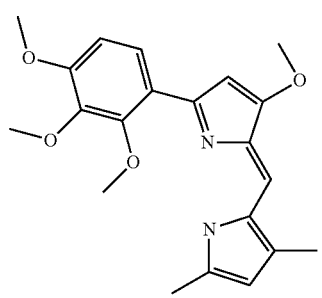

3-methoxy-5-(2,3,4-trimethoxyphenyl)-2-
((3,5-dimethyl-1H-pyrrol-2-yl)methylene)-
2H-pyrrole

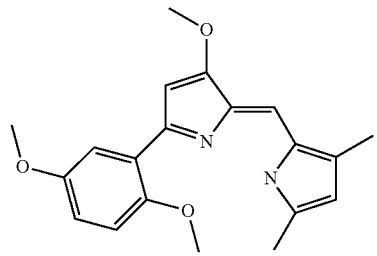

3-methoxy-5-(3,4-dimethoxyphenyl)-2-((3,5-
dimethyl-1H-pyrrol-2-yl)methylene)-2H-
pyrrole

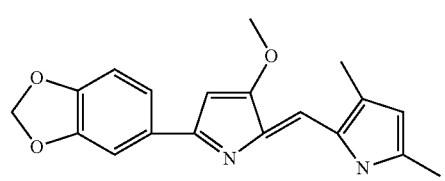

2-((5-(benzo[d][1,3]dioxol-5-yl)-3-methoxy-
2H-pyrrol-2-ylidene)methyl)-3,5-dimethyl-
1H-pyrrole

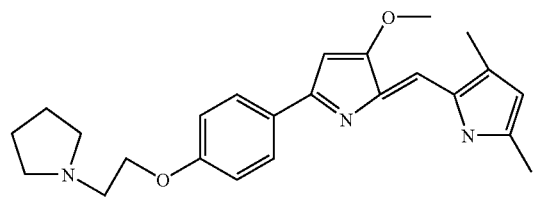

2-((5-(4-(2-(pyrrolidin-1-yl)ethoxy)phenyl)-
3-methoxy-2H-pyrrol-2-ylidene)methyl)-3,5-
dimethyl-1H-pyrrole -continued

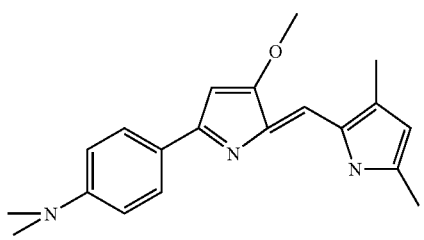

22

4-(4-methoxy-5-((3,5-dimethyl-1H-pyrrol-2-yl)methylene)-5H-pyrrol-2-yl)-N,N-dimethylbenzenamine

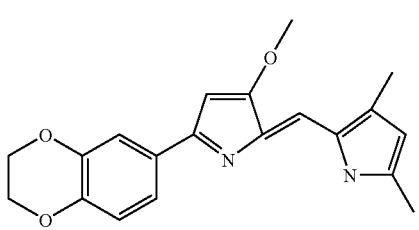

23

2-((5-(2,3-dihydrobenzo[b][1,4]dioxin-7-yl)-3-methoxy-2H-pyrrol-2-ylidene)methyl)-3,5-dimethyl-1H-pyrrole

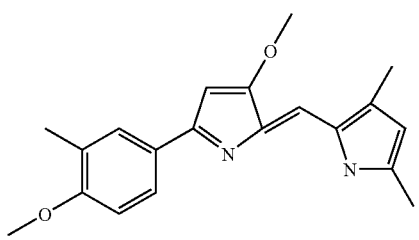

24

2-((3-methoxy-5-(4-methoxy-3-methylphenyl)-2H-pyrrol-2-ylidene)methyl)-3,5-dimethyl-1H-pyrrole

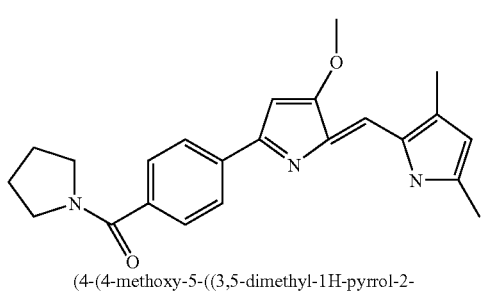

25

(4-(4-methoxy-5-((3,5-dimethyl-1H-pyrrol-2-yl)methylene)-5H-pyrrol-2-yl)phenyl)(pyrrolidin-1-yl)methanone

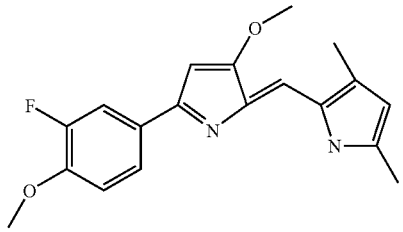

26

2-((5-(3-fluoro-4-methoxyphenyl)-3-methoxy-2H-pyrrol-2-ylidene)methyl)-3,5-dimethyl-1H-pyrrole -continued

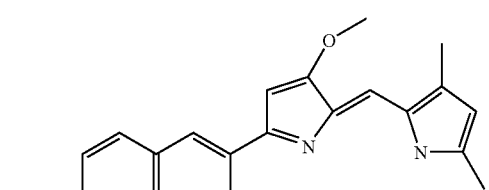

27

2-((3-methoxy-5-(2-methoxynaphtalen-6-yl)-2H-pyrrol-2-ylidene)methyl)-3,5-dimethyl-1H-pyrrole

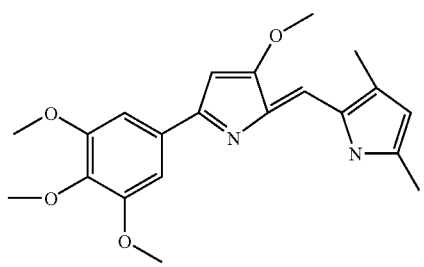

28

2-((3-methoxy-5-(3,4,5-trimethoxyphenyl)-2H-pyrrol-2-ylidene)methyl)-3,5-dimethyl-1H-pyrrole

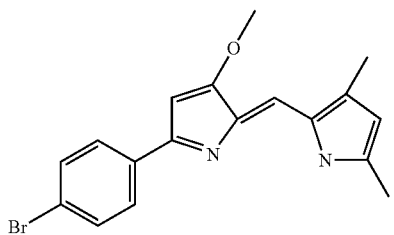

29

2-((5-(4-bromophenyl)-3-methoxy-2H-pyrrol-2-ylidene)methyl)-3,5-dimethyl-1H-pyrrole

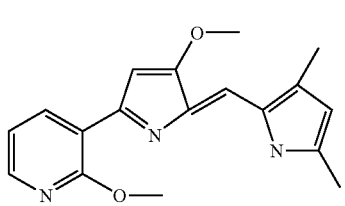

30

2-methoxy-3-(4-methoxy-5-((3,5-dimethyl-1H-pyrrol-2-yl)methylene)-5H-pyrrol-2-yl)pyridine

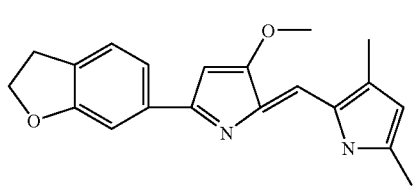

31

2-((5-(2,3-dihydrobenzofuran-6-yl)-3-methoxy-2H-pyrrol-2-ylidene)methyl)-3,5-dimethyl-1H-pyrrole

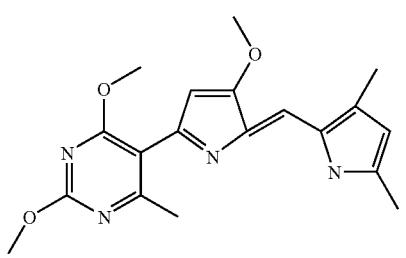

2,4-dimethoxy-5-(4-methoxy-5-((3,5-dimethyl-1H-pyrrol-2-yl)methylene)-5H-pyrrol-2-yl)pyrimidine

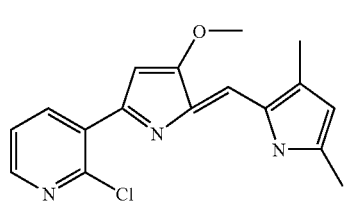

2-chloro-3-(4-methoxy-5-((3,5-dimethyl-1H-pyrrol-2-yl)methylene)-5H-pyrrol-2-yl)pyridine

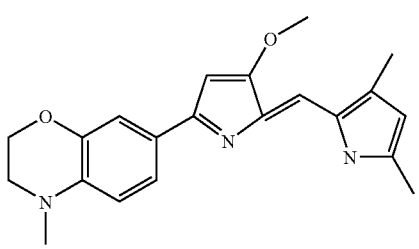

3,4-dihydro-7-(4-methoxy-5-((3,5-dimethyl-1H-pyrrol-2-yl)methylene)-5H-pyrrol-2-yl)-4-methyl-2H-benzo[b][1,4]oxazine

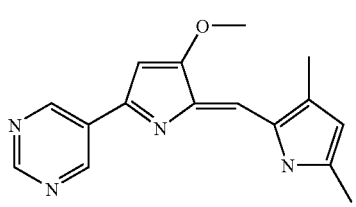

5-(4-methoxy-5-((3,5-dimethyl-1H-pyrrol-2-yl)methylene)-5H-pyrrol-2-yl)pyrimidine

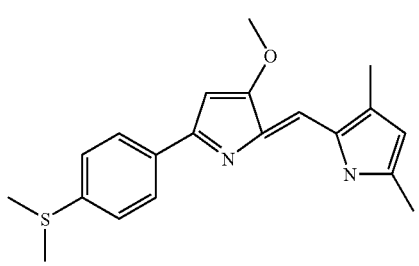

2-((5-(4-(isopropylthio)phenyl)-3-methoxy-2H-pyrrol-2-ylidene)methyl)-3,5-dimethyl-1H-pyrrole

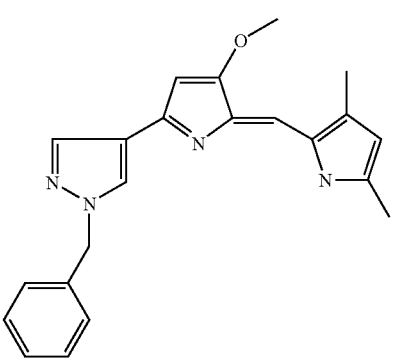

1-benzyl-4-(4-methoxy-5-((3,5-dimethyl-1H-pyrrol-2-yl)methylene-5H-pyrrol-2-yl)-1H-pyrazole

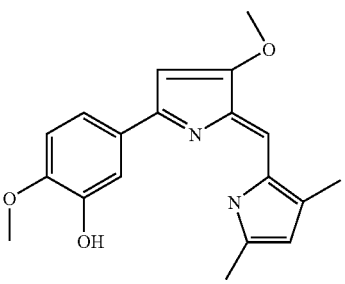

2-methoxy-5-(4-methoxy-5-((3,5-dimethyl-1H-pyrrol-2-yl)methylene)-5H-pyrrol-2-yl)phenol

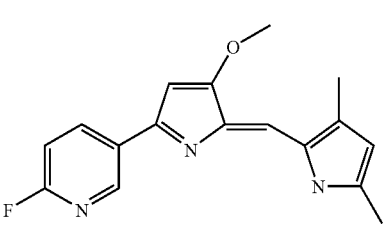

2-fluoro-5-(4-methoxy-5-((3,5-dimethyl-1H-pyrrol-2-yl)methylene)-5H-pyrrol-2-yl)pyridine

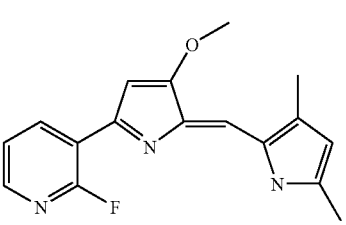

2-fluoro-3-(4-methoxy-5-((3,5-dimethyl-1H-pyrrol-2-yl)methylene)-5H-pyrrol-2-yl)pyridine

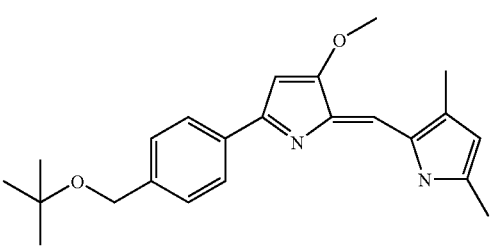

5-(4-(tert-butoxymethyl)phenyl)-3-methoxy-2-((3,5-dimethyl-1H-pyrrol-2-yl)methylene)-2H-pyrrole

42

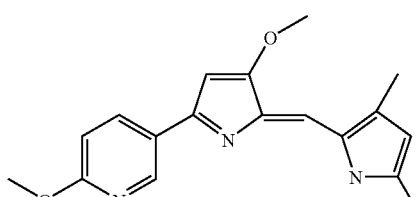

2-methoxy-5-(4-methoxy-5-((3,5-dimethyl-
1H-pyrrol-2-yl)methylene)-5H-pyrrol-2-
yl)pyridine

43

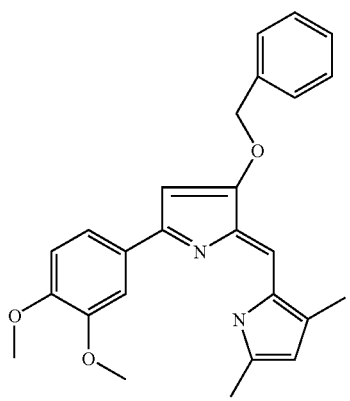

3-(benzyloxy)-5-(3,4-dimethoxyphenyl)-2-
((3,5-dimethyl-1H-pyrrol-2-yl)methylene)-
2H-pyrrole

44

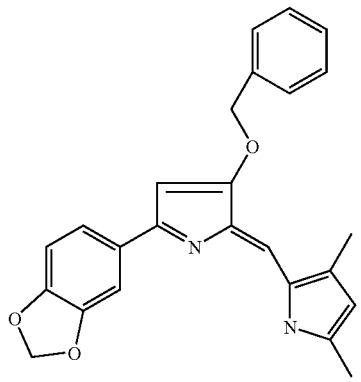

5-(benzo[d][1,3]dioxol-5-yl)-3-(benzyloxy)-
2-((3,5-dimethyl-1H-pyrrol-2-yl)methylene)-
2H-pyrrole or pharmaceutically acceptable salts thereof.

5.4 Pharmaceutical Compositions

Dipyrrole Compounds that can be used to formulate the pharmaceutical compositions of the invention are Dipyrrole Compounds of Formula (Ia) or Dipyrrole Compounds of Formula (Ib) or Dipyrrole Compounds selected from Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 or pharmaceutically acceptable salts thereof.

The invention provides pharmaceutical compositions comprising an effective amount Dipyrrole Compound and a pharmaceutically acceptable carrier. In one aspect, the invention provides a pharmaceutical composition comprising an effective amount of a Dipyrrole Compound and a pharmaceutically acceptable carrier. In further aspects, the invention provides a pharmaceutical composition comprising an effective amount of a Dipyrrole Compound and an effective amount of a compound other than the Dipyrrole Compound. In certain aspects, the pharmaceutical composition comprises a combination of different Dipyrrole Compounds.

In one embodiment, the invention provides a composition comprising a pharmaceutically acceptable carrier and an effective amount Compound 17, Compound 22, or Compound 37 or a pharmaceutically acceptable salt thereof. In a more specific embodiment, the pharmaceutically acceptable salt is a mesylate salt.

5.5 Methods for Treating Cancer and Viral Diseases Using Dipyrrole Compounds Dipyrrole Compounds that can be used with the methods of the invention are Dipyrrole Compounds of Formula (Ia) or Dipyrrole Compounds of Formula (Ib) or Dipyrrole Compounds selected from Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 or pharmaceutically acceptable salts thereof.

The invention provides a method for treating cancer or a neoplastic disease in a subject in need of treatment, wherein the method comprises administering to the subject an effective amount of a Dipyrrole Compound or a pharmaceutically acceptable salt thereof.

The invention also provides a method for treating cancer or a neoplastic disease in a subject in need of treatment of cancer or a neoplastic disease, wherein the method comprises administering to the subject (i) an effective amount of a Dipyrrole Compound or a pharmaceutically acceptable salt thereof; and (ii) a pharmaceutically acceptable carrier. The invention also provides a method for treating cancer or a neoplastic disease in a subject in need of treatment of cancer or a neoplastic disease, wherein the method comprises administering to the subject (i) an effective amount of a Dipyrrole Compound or a pharmaceutically acceptable salt thereof; (ii) a pharmaceutically acceptable carrier; and (iii) a therapeutic agent other than the Dipyrrole Compound, such as another chemotherapeutic agent. Combinations of different Dipyrrole Compounds may also be administered to treat the cancer or the neoplastic disease.

The invention provides methods for inhibiting or reducing the growth of a cancer cell or neoplastic cell, wherein the method comprises contacting the cancer cell or the neoplastic cell with an effective amount of a Dipyrrole Compound or a pharmaceutically acceptable salt thereof.

The invention further provides a method for treating a viral infection in a subject in need of treatment of a viral infection, wherein the method comprises administering to the subject (i) an effective amount of a Dipyrrole Compound or a pharmaceutically acceptable salt thereof; and (ii) a pharmaceutically acceptable carrier. The invention also provides a method for treating a viral infection in a subject in need of treatment of a viral infection, wherein the method comprises administering to the subject (i) an effective amount of a Dipyrrole Compound or a pharmaceutically acceptable salt thereof; (ii) a pharmaceutically acceptable carrier; and (iii) a therapeutic agent other than a Dipyrrole Compound, such as another antiviral agent. Combinations of different Dipyrrole Compounds may also be administered to treat viral infections.

The invention also provides methods for inhibiting or reducing the replication or infectivity of a virus, wherein the method comprises contacting a cell infected with the virus with an effective amount of a Dipyrrole Compound or a pharmaceutically acceptable salt thereof. The invention also provides methods for inhibiting or reducing the propagation of a virus-infected cell, wherein the method comprises contacting the virus-infected cell with a Dipyrrole Compound or a pharmaceutically acceptable salt thereof.

In other embodiments, a compound useful in the present methods is Compound 17, Compound 22, or Compound 37 or a pharmaceutically acceptable salt thereof. In a specific embodiment, the pharmaceutically acceptable salt is a mesylate salt.

5.6 Methods for Making the Dipyrrole Compounds

The invention further provides methods useful for making Dipyrrole Compounds.

The compounds of the invention can be obtained via standard, well-known synthetic methodology, see e.g. March, J. *Advanced Organic Chemistry; Reactions Mechanisms, and Structure*, 4$^{th}$ ed., 1992. Illustrative methods are described below. Starting materials useful for preparing the compounds of the invention and intermediates therefore, are commercially available or can be prepared from commercially available materials using known synthetic methods and reagents.

An example of a synthetic pathways useful for making the Dipyrrole Compounds is set forth below and generalized in Scheme 1.

The Dipyrrole Compounds can be obtained via conventional organic synthesis, e.g., as described below. Scheme 1 indicates a general method by which the Dipyrrole Compounds of Formula (Ib) can be obtained, wherein $R_7$ and $R_9$ are defined above for the Dipyrrole Compounds of Formula (Ib).

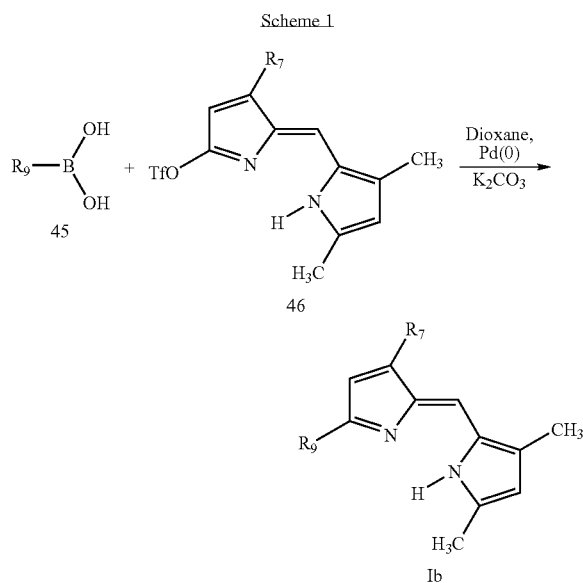

Referring to Scheme 1, to a solution of the triflate (46) (1 mmol) and boronic acid (45) (2 mmol) in anhydrous dioxane (25 mL), 4M solution of $K_2CO_3$ (8 mmol) is added. The solution is degassed for 10 min and then Palladium (0) (0.010 mmol) is added. The reaction mixture is heated at 90-95° C. for 3 hours. The reaction mixture is cooled to room temperature and is extracted with ethyl acetate. The organic layer is washed with brine and water. The organic layer is separated, dried over anhydrous sodium sulphate and filtered. The filtrate is evaporated to obtain a crude residue and passed through silica gel column chromatography to get the product (a compound of Formula (Ib)).

The experimental procedure for more specific Dipyrrole Compounds is shown in Scheme 2:

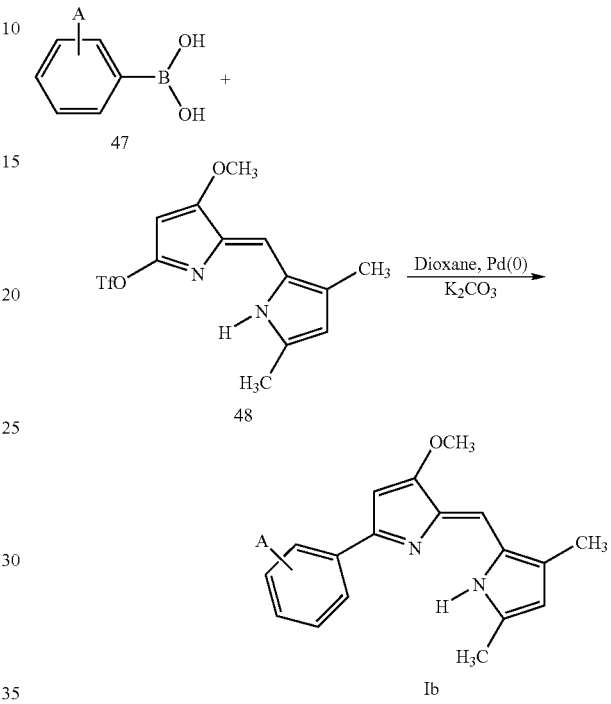

Referring to Scheme 2, to a solution of the triflate (48) (1 mmol) and boronic acid (47) (2 mmol) in anhydrous dioxane (25 mL), 4M solution of $K_2CO_3$ (8 mmol) is added. The solution is degassed for 10 min and then Palladium (0) (0.010 mmol) is added. The reaction mixture is heated at 90-95° C. for 3 hours. The reaction mixture is cooled to room temperature and is extracted with ethyl acetate. The organic layer is washed with brine and water. The organic layer is separated, dried over anhydrous sodium sulphate and filtered. The filtrate is evaporated to obtain a crude residue and passed through silica gel column chromatography to get the product (a compound of Formula (Ib)).

5.7 Therapeutic/Prophylactic Administration and Compositions

Due to their activity, the Dipyrrole Compounds are advantageously useful in veterinary and human medicine. For example, the Dipyrrole Compounds are useful for the treatment or prevention of cancer or neoplastic disease or inhibiting the growth of a cancer cell or neoplastic cell. The Dipyrrole Compounds are also useful for the treatment or prevention of a viral infection or inhibiting the replication or infectivity of a virus.

Dipyrrole Compounds include the compounds of Formula (Ia), Formula (Ib), Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44.

The invention provides methods of treatment and prophylaxis by administration to a patient of an effective amount of a Dipyrrole Compound. The patient is an animal, including, but not limited, a human, mammal, or non-human animal such as a cow, horse, sheep, pig, chicken, turkey, quail, cat, dog, mouse, rat, rabbit, mouse or guinea pig, and is more preferably a mammal, and most preferably a human.

The present compositions, which comprise an effective amount of a Dipyrrole Compound, can be administered by any convenient route, for example by infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer a Dipyrrole Compound. In certain embodiments, more than one Dipyrrole Compound is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically to the ears, nose, eyes, or skin. The preferred mode of administration is left to the discretion of the practitioner, and will depend in-part upon the site of the medical condition (such as the site of cancer or viral infection).

In specific embodiments, it may be desirable to administer one or more Dipyrrole Compounds locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a viral infection, tissue or organ transplant, or autoimmune response.

In certain embodiments, it may be desirable to introduce one or more Dipyrrole Compounds into the central nervous system by any suitable route, including intraventricular and intrathecal injection. Intraventricular injection may be facilitated by an intraventricular catheter, for example, attached to a reservoir, such as an Ommaya reservoir.

Pulmonary administration can also be employed, e.g. by use of an inhaler or nebulizer, and formulating with an aerosolizing agent, or via perfusion in a fluorocarbon or synthetic pulmonary surfactant. In certain embodiments, the Dipyrrole Compounds can be formulated as a suppository, with traditional binders and carriers such as triglycerides.

In another embodiment, the Dipyrrole Compounds can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the Dipyrrole Compounds can be delivered in a controlled-release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled-release system can be placed in proximity of the target of the Dipyrrole Compounds, e.g., the brain, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) may be used.

The present compositions comprise an effective amount of a Dipyrrole Compound and a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which a Dipyrrole Compound is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, auxiliary, stabilizing, thickening, lubricating and coloring agents may be used. When administered to a patient, the Dipyrrole Compounds and pharmaceutically acceptable carriers can be sterile. In one embodiment, water is a carrier when the Dipyrrole Compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release Formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in "Remington's Pharmaceutical Sciences" by E.W. Martin.

The phrase "pharmaceutically acceptable salt(s)," as used herein includes but are not limited to salts of acidic or basic groups that may be present in compounds used in the present compositions. Dipyrrole Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, mesylate, hydroxyethyl sulfonate, and pamoate (i.e., 1,1'-methylene-bis-(2-hydroxy-3-naphthoate)) salts. Dipyrrole Compounds included in the present compositions that include an amino moiety may form pharmaceutically acceptable salts with various amino acids, in addition to the acids mentioned above. Compounds, included in the present compositions, that are acidic in nature are capable of forming base salts with various pharmacologically or cosmetically acceptable cations. Examples of such salts include alkali metal or alkaline earth metal salts and, particularly, calcium, magnesium, sodium lithium, zinc, potassium, and iron salts.

In another embodiment, the Dipyrrole Compounds are formulated in accordance with routine procedures as a pharmaceutical composition adapted for intravenous administration to human beings. Typically, Dipyrrole Compounds for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the Dipyrrole Compound is to be administered by infusion, it can be dispensed, for example, with an infusion bottle containing sterile pharmaceutical grade water or saline. Where the Dipyrrole Compound is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered Dipyrrole Compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate may also be used. Oral compositions can include standard carriers such as mannitol, lactose, starch, magnesium stearate, sodium saccharine, cellulose, or magnesium carbonate. Such carriers can be of pharmaceutical grade.

The amount of the Dipyrrole Compound that will be effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable effective dosage ranges for intravenous administration are generally about 0.1 to about 5 mg, preferably about 0.5 to about 3 mg of Dipyrrole Compound per kilogram body weight. In specific embodiments, the i.v. dose is about 0.1 to about 0.5 mg/kg, about 0.3 to about 0.8 mg/kg, about 0.8 to about 1.2 mg/kg, about 1.2 to about 2.0 mg/kg, or about 2.0 to about 3.0 mg/kg (or the equivalent doses expressed per square meter of body surface area). Alternatively, a suitable dose range for i.v. administration may be obtained using doses of about 8 to about 500 mg, without adjustment for a patient's body weight or body surface area. Suitable dosage ranges for intranasal administration are generally about 0.01 pg/kg body weight to 1 mg/kg body weight. Suppositories generally contain 0.5% to 10% by weight of one or more Dipyrrole Compounds alone or in combination with another therapeutic agent. Oral compositions can contain about 10% to about 95% by weight of one or more Dipyrrole Compounds alone or in combination with another therapeutic agent. In specific embodiments of the invention, suitable dose ranges for oral administration are generally about 0.1 to about 20 mg, preferably about 0.5 to about 10 mg, and more preferably about 1 to about 5 mg of Dipyrrole Compound per kilogram body weight or their equivalent doses expressed per square meter of body surface area. In specific embodiments the oral dose is about 1 to about 7.5 mg/kg, about 7.5 to about 10 mg/kg, about 10 to about 12.5 mg/kg, about 12.5 to about 15 mg/kg, or about 15 to about 20 mg/kg (or the equivalent doses expressed per square meter of body surface area). In another embodiment, a suitable dose range for oral administration, from about 20 to about 2000 mg, without adjustment for a patient's body weight or body surface area. Other effective doses may be extrapolated from dose-response curves derived from in vitro or animal model test systems. Such animal models and systems are well known in the art.

The invention also provides pharmaceutical packs or kits comprising one or more containers containing one or more Dipyrrole Compounds. Optionally associated with such container(s) can be a notice in the form prescribed by a governmental agency regulating the manufacture, use or sale of pharmaceuticals or biological products, which notice reflects approval by the agency of manufacture, use or sale for human administration. In certain embodiments, e.g., when administered for the treatment or prevention of cancer, the kit may also contain one or more chemotherapeutic agents useful for treating cancer or a neoplastic disease to be administered in combination with a Dipyrrole Compound.

The Dipyrrole Compounds are preferably assayed in vitro, and then in vivo, for the desired therapeutic or prophylactic activity, prior to use in humans. For example, in vitro assays can be used to determine whether administration of a specific Dipyrrole Compound or combination of Dipyrrole Compounds is preferred.

In one embodiment, a patient tissue sample is grown in culture, and contacted or otherwise administered with a Dipyrrole Compound, and the effect of such Dipyrrole Compound upon the tissue sample is observed and compared to a non-contacted tissue. In other embodiments, a cell culture model is used in which the cells of the cell culture are contacted or otherwise administered with a Dipyrrole Compound, and the effect of such Dipyrrole Compound upon the cell culture sample is observed and compared to a non-contacted cell culture. Generally, a lower level of proliferation or survival of the contacted cells compared to the non-contracted cells indicates that the Dipyrrole Compound is effective to treat the patient. Such Dipyrrole Compounds may also be demonstrated effective and safe using animal model systems.

Other methods will be known to the skilled artisan and are within the scope of the invention.

5.8 Inhibition of Cancer and Neoplastic Disease

The Dipyrrole Compounds may be demonstrated to inhibit tumor cell proliferation, cell transformation and tumorigenesis in vitro and in vivo using a variety of assays known in the art, or described herein. Such assays may use cells of a cancer cell line, or cells from a patient. Many assays well-known in the art can be used to assess such survival and/or growth; for example, cell proliferation can be assayed by measuring ($^3$H)-thymidine incorporation, by direct cell count, by detecting changes in transcription, translation or activity of known genes such as proto-oncogenes (e.g., fos, myc) or cell-cycle markers (Rb, cdc2, cyclin A, D1, D2, D3, E, etc). The levels of such protein and mRNA and activity can be determined by any method well known in the art. For example, protein can be quantitated by known immunodiagnostic methods such as Western blotting or immunoprecipitation using commercially available antibodies (for example, many cell cycle marker antibodies are from Santa Cruz Inc.). mRNA can be quantitated by methods that are well known and routine in the art, for example by northern analysis, RNase protection, the polymerase chain reaction in connection with the reverse transcription, etc. Cell viability can be assessed by using trypan-blue staining or other cell death or viability markers known in the art. Differentiation can be assessed visually based on changes in morphology, etc.

The present invention provides for cell cycle and cell proliferation analysis by a variety of techniques known in the art, including but not limited to the following:

As one example, bromodeoxyuridine (BRDU) incorporation may be used as an assay to identify proliferating cells. The BRDU assay identifies a cell population undergoing DNA synthesis by incorporation of BRDU into newly synthesized DNA. Newly synthesized DNA may then be detected using an anti-BRDU antibody (see Hoshino et al., 1986, Int. J. Cancer 38, 369; Campana et al., 1988, J. Immunol. Meth. 107, 79).

Cell proliferation may also be examined using (3H)-thymidine incorporation (see e.g., Chen, J., 1996, Oncogene 13:1395-403; Jeoung, J., 1995, J. Biol. Chem. 270:18367-73). This assay allows for quantitative characterization of S-phase DNA synthesis. In this assay, cells synthesizing DNA will incorporate ($^3$H)-thymidine into newly synthesized DNA. Incorporation may then be measured by standard techniques in the art such as by counting of radioisotope in a Scintillation counter (e.g. Beckman LS 3800 Liquid Scintillation Counter).

Detection of proliferating cell nuclear antigen (PCNA) may also be used to measure cell proliferation. PCNA is a 36 kilodalton protein whose expression is elevated in proliferating cells, particularly in early G1 and S phases of the cell cycle and therefore may serve as a marker for proliferating cells. Positive cells are identified by immunostaining using an anti-PCNA antibody (see Li et al., 1996, Curr. Biol. 6:189-199; Vassilev et al., 1995, J. Cell Sci. 108:1205-15).

Cell proliferation may be measured by counting samples of a cell population over time (e.g. daily cell counts). Cells may be counted using a hemacytometer and light microscopy (e.g. HyLite hemacytometer, Hausser Scientific). Cell number may be plotted against time in order to obtain a growth curve for the population of interest. In a specific embodiment, cells counted by this method are first mixed with the dye Trypan-blue (Sigma), such that living cells exclude the dye, and are counted as viable members of the population.

DNA content and/or mitotic index of the cells may be measured, for example, based on the DNA ploidy value of the cell. For example, cells in the G1 phase of the cell cycle generally contain a 2N DNA ploidy value. Cells in which DNA has been replicated but have not progressed through mitosis (e.g. cells in S-phase) will exhibit a ploidy value higher than 2N and up to 4N DNA content. Ploidy value and cell-cycle kinetics may be further measured using propidium iodide assay (see e.g. Turner, T., et al., 1998, Prostate 34:175-81). Alternatively, the DNA ploidy may be determined by quantitation of DNA Feulgen staining (which binds to DNA in a stoichiometric manner) on a computerized microdensitometrystaining system (see e.g., Bacus, S., 1989, Am. J. Pathol. 135:783-92). In an another embodiment, DNA content may be analyzed by preparation of a chromosomal spread (Zabalou, S., 1994, Hereditas. 120:127-40; Pardue, 1994, Meth. Cell Biol. 44:333-351).

The cell count in a culture can be determined by, e.g., measuring the intracellular level of ATP. Intracellular ATP levels have previously been shown to correlate to cell number (Crouch, Kozlowski et al. (1993), J Immunol Methods 160 (1):81-8. After 3 days of treatment, intracellular ATP can be measured using, e.g., the ViaLight kit (BioWhittaker) according to the manufacturer's instructions.

The expression of cell-cycle proteins (e.g., CycA. CycB, CycE, CycD, cdc2, Cdk4/6, Rb, p21, p27, etc.) provide crucial information relating to the proliferative state of a cell or population of cells. For example, identification in an anti-proliferation signaling pathway may be indicated by the induction of p21$^{cip1}$. Increased levels of p21 expression in cells results in delayed entry into G1 of the cell cycle (Harper et al., 1993, Cell 75:805-816; Li et al., 1996, Curr. Biol. 6:189-199). p21 induction may be identified by immunostaining using a specific anti-p21 antibody available commercially (e.g. Santa Cruz). Similarly, cell-cycle proteins may be examined by Western blot analysis using commercially available antibodies. In another embodiment, cell populations are synchronized prior to detection of a cell cycle protein. Cell cycle proteins may also be detected by FACS (fluorescence-activated cell sorter) analysis using antibodies against the protein of interest.

Detection of changes in length of the cell cycle or speed of cell cycle may also be used to measure inhibition of cell proliferation by the Dipyrrole Compounds of the Invention. In one embodiment the length of the cell cycle is determined by the doubling time of a population of cells (e.g., using cells contacted or not contacted with one or more Dipyrrole Compounds). In another embodiment, FACS analysis is used to analyze the phase of cell cycle progression, or purify G1, S, and G2/M fractions (see e.g., Delia, D. et al., 1997, Oncogene 14:2137-47).

Lapse of cell cycle checkpoint(s), and/or induction of cell cycle checkpoint(s), may be examined by the methods described herein, or by any method known in the art. Without limitation, a cell cycle checkpoint is a mechanism which ensures that a certain cellular events occur in a particular order. Checkpoint genes are defined by mutations that allow late events to occur without prior completion of an early event (Weinert, T., and Hartwell, L., 1993, Genetics, 134:63-80). Induction or inhibition of cell cycle checkpoint genes may be assayed, for example, by Western blot analysis, or by immunostaining, etc. Lapse of cell cycle checkpoints may be further assessed by the progression of a cell through the checkpoint without prior occurrence of specific events (e.g. progression into mitosis without complete replication of the genomic DNA).

In addition to the effects of expression of a particular cell cycle protein, activity and post-translational modifications of proteins involved in the cell cycle can play an integral role in the regulation and proliferative state of a cell. The invention provides for assays involved in detecting post-translational modifications (e.g. phosphorylation) by any method known in the art. For example, antibodies that detect phosphorylated tyrosine residues are commercially available, and may be used in Western blot analysis to detect proteins with such modifications. In another example, modifications such as myristylation, may be detected on thin layer chromatography or reverse phase h.p.l.c. (see e.g., Glover, C., 1988, Biochem. J. 250:485-91; Paige, L., 1988, Biochem J.; 250:485-91).

Activity of signaling and cell cycle proteins and/or protein complexes is often mediated by a kinase activity. Thus, analysis of kinase activity by assays such as the histone H1 assay can be used to evaluate the proliferative state of a cell (see e.g., Delia, D. et al., 1997, Oncogene 14:2137-47).

The Dipyrrole Compounds can also be demonstrated to alter cell proliferation in cultured cells in vitro using methods which are well known in the art; Specific examples of cell culture models include, but are not limited to, for lung cancer, primary rat lung tumor cells (Swafford et al., 1997, Mol. Cell. Biol., 17:1366-1374) and large-cell undifferentiated cancer cell lines (Mabry et al., 1991, Cancer Cells, 3:53-58); colorectal cell lines for colon cancer (Park and Gazdar, 1996, J. Cell Biochem. Suppl. 24:131-141); multiple established cell lines for breast cancer (Hambly et al., 1997, Breast Cancer Res. Treat. 43:247-258; Gierthy et al., 1997, Chemosphere 34:1495-1505; Prasad and Church, 1997, Biochem. Biophys. Res. Commun. 232:14-19); a number of well-characterized cell models for prostate cancer (Webber et al., 1996, Prostate, Part 1, 29:386-394; Part 2, 30:58-64; and Part 3. 30:136-142; Boulikas, 1997, Anticancer Res. 17:1471-1505); for genitourinary cancers, continuous human bladder cancer cell lines (Ribeiro et al., 1997, Int. J. Radiat. Biol. 72:11-20); organ cultures of transitional cell carcinomas (Booth et al., 1997, Lab Invest. 76:843-857) and rat progression models (Vet et al., 1997, Biochim. Biophys Acta 1360:39-44); and established cell lines for leukemias and lymphomas (Drexler, 1994, Leuk. Res. 18:919-927, Tohyama, 1997, Int. J. Hematol. 65:309-317).

The Dipyrrole Compounds can also be demonstrated to inhibit cell transformation (or progression to malignant phenotype) in vitro. In this embodiment, cells with a transformed cell phenotype are contacted with one or more Dipyrrole Compounds, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, *General Virology*, 3d Ed., John Wiley & Sons, New York, pp. 436-446).

In one embodiment, the Dipyrrole Compounds are cytotoxic in cancer cells or neoplastic cells.

In another embodiment, the Dipyrrole Compounds demonstrate a higher level of cytotoxicity in cancer cells than in non-cancer cells.

Loss of invasiveness or decreased adhesion may also be used to demonstrate the anti-cancer effects of the Dipyrrole Compounds. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state. Loss of invasiveness may be measured by a variety of techniques known in the art including, for example, induction of E-cadherin-mediated cell-cell adhesion. Such E-cadherin-mediated adhesion can result in phenotypic reversion and loss of invasiveness (Hordijk et al., 1997, Science 278:1464-66).

Loss of invasiveness may further be examined by inhibition of cell migration. A variety of 2-dimensional and 3-dimensional cellular matrices are commercially available (Calbiochem-Novabiochem Corp. San Diego, Calif.). Cell migration across or into a matrix may be examined by microscopy, time-lapsed photography or videography, or by any method in the art allowing measurement of cellular migration. In a related embodiment, loss of invasiveness is examined by response to hepatocyte growth factor (HGF). HGF-induced cell scattering is correlated with invasiveness of cells such as Madin-Darby canine kidney (MDCK) cells. This assay identifies a cell population that has lost cell scattering activity in response to HGF (Hordijk et al., 1997, Science 278:1464-66).

Alternatively, loss of invasiveness may be measured by cell migration through a chemotaxis chamber (Neuroprobe/Precision Biochemicals Inc. Vancouver, BC). In such an assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated may then be correlated with invasiveness (see e.g., Ohnishi, T., 1993, Biochem. Biophys. Res. Commun. 193: 518-25).

The Dipyrrole Compounds can also be demonstrated to inhibit tumor formation in vivo. A vast number of animal models of hyperproliferative disorders, including tumorigenesis and metastatic spread, are known in the art (see Table 317-1, Chapter 317, "Principals of Neoplasia," in *Harrison's Principals of Internal Medicine, 13th Edition*, Isselbacher et al., eds., McGraw-Hill, New York, p. 1814, and Lovejoy et al., 1997, J. Pathol. 181:130-135). Specific examples include for lung cancer, transplantation of tumor nodules into rats (Wang et al., 1997, Ann. Thorac. Surg. 64:216-219) or establishment of lung cancer metastases in SCID mice depleted of NK cells (Yono and Sone, 1997, Gan To Kagaku Ryoho 24:489-494); for colon cancer, colon cancer transplantation of human colon cancer cells into nude mice (Gutman and Fidler, 1995, World J. Surg. 19:226-234), the cotton top tamarin model of human ulcerative colitis (Warren, 1996, Aliment. Pharmacol. Ther. 10 Supp 12:45-47) and mouse models with mutations of the adenomatous polyposis tumor suppressor (Polakis, 1997, Biochim. Biophys. Acta 1332:F127-F147); for breast cancer, transgenic models of breast cancer (Dankort and Muller, 1996, Cancer Treat. Res. 83:71-88; Amundadittir et al., 1996, Breast Cancer Res. Treat. 39:119-135) and chemical induction of tumors in rats (Russo and Russo, 1996, Breast Cancer Res. Treat. 39:7-20); for prostate cancer, chemically-induced and transgenic rodent models, and human xenograft models (Royai et al., 1996, Semin. Oncol. 23:35-40); for genitourinary cancers, induced bladder neoplasm in rats and mice (Oyasu, 1995, Food Chem. Toxicol 33:747-755) and xenografts of human transitional cell carcinomas into nude rats (Jarrett et al., 1995, J. Endourol. 9:1-7); and for hematopoietic cancers, transplanted allogeneic marrow in animals (Appelbaum, 1997, Leukemia 11 (Suppl. 4):S15-S17). Further, general animal models applicable to many types of cancer have been described, including, but not restricted to, the p53-deficient mouse model (Donehower, 1996, Semin. Cancer Biol. 7:269-278), the Min mouse (Shoemaker et al., 1997, Biochem. Biophys. Acta, 1332:F25-F48), and immune responses to tumors in rat (Frey, 1997, Methods, 12:173-188).

For example, a Dipyrrole Compound can be administered to a test animal, preferably a test animal predisposed to develop a type of tumor, and the test animal subsequently examined for a decreased incidence of tumor formation in comparison with controls to which are not administered the Dipyrrole Compound. Alternatively, a Dipyrrole Compound can be administered to test animals having tumors (e.g., animals in which tumors have been induced by introduction of malignant, neoplastic, or transformed cells, or by administration of a carcinogen) and subsequently examining the tumors in the test animals for tumor regression in comparison to controls to which the Dipyrrole Compound has not been administered.

Certain animal models for human cancers involve the injection of the human cancer cells into an immune-deficient mouse (e.g., a SCID mouse or a nude mouse). For example, PC3 human prostate cancer cells can be injected into nude mice to generate an animal model for prostate cancer (Angelucci et al., 2004, Int. J. Oncol. 25(6)1713-1720). In another example, cervical cancer cell lines such as CaSki, SiHa, HeLa, HeLaS3, C33A, and HT3 can be injected into nude mice to generate an animal model for cervical cancer (e.g., Ahn et al., 2004, Gynecol Oncol. 92(2):611-621).

5.9 Treatment or Prevention of Cancer or a Neoplastic Disease Further Comprising Administering Chemotherapy or Radiotherapy Cancer or a neoplastic disease, including, but not limited to, neoplasms, tumors, metastases, or any disease or disorder characterized by uncontrolled cell growth, can be treated or prevented by administration of an effective amount of a Dipyrrole Compound.

In certain embodiments, the present methods for treating or preventing cancer or neoplastic disease further comprise administering an anti-cancer, chemotherapeutic agent including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In another embodiment, the anti-cancer agents is one or more of those presented below in Table 1.

TABLE 1

| | |
|---|---|
| Radiation: | γ-radiation |
| Alkylating agents | |
| Nitrogen mustards: | cyclophosphamide |
| | Ifosfamide |
| | Trofosfamide |
| | Chlorambucil |
| Nitrosoureas: | carmustine (BCNU) |
| | Lomustine (CCNU) |
| Alkylsulphonates: | Busulfan |
| | Treosulfan |

TABLE 1-continued

| | |
|---|---|
| Triazenes: | Dacarbazine |
| Platinum containing compounds: | Cisplatin |
| | Carboplatin |
| | Oxaliplatin |
| Plant Alkaloids | |
| Vinca alkaloids: | Vincristine |
| | Vinblastine |
| | Vindesine |
| | Vinorelbine |
| Taxoids: | Paclitaxel |
| | Docetaxol |
| DNA Topoisomerase Inhibitors | |
| Epipodophyllins: | Etoposide |
| | Teniposide |
| | Topotecan |
| | 9-aminocamptothecin |
| | campto irinotecan |
| | crisnatol |
| mitomycins: | |
| mitomycin C | Mitomycin C |
| Anti-metabolites | |
| Anti-folates: | |
| DHFR inhibitors: | methotrexate |
| | Trimetrexate |
| IMP dehydrogenase Inhibitors: | mycophenolic acid |
| | Tiazofurin |
| | Ribavirin |
| | EICAR |
| Ribonucleotide reductase Inhibitors: | Hydroxyurea |
| | Deferoxamine |
| Pyrimidine analogs: | |
| Uracil analogs 5-Fluorouracil | Floxuridine |
| | Doxifluridine |
| | Ratitrexed |
| Cytosine analogs | cytarabine (ara C) |
| | Cytosine arabinoside |
| | Fludarabine |
| Purine analogs: | mercaptopurine |
| | Thioguanine |
| Hormonal therapies: | |
| Receptor antagonists: | Raloxifene |
| Anti-estrogens Tamoxifen | Megestrol |
| LHRH agonists: | Goserelin |
| | Leuprolide acetate |
| Anti-androgens: | Flutamide |
| | Bicalutamide |
| Retinoids/Deltoids | |
| Vitamin D3 analogs: | EB 1089 |
| | CB 1093 |
| | KH 1060 |
| Photodyamic therapies: | Vertoporfin (BPD-MA) |
| | Phthalocyanine |
| | photosensitizer Pc4 |
| | Demethoxy-hypocrellin A |
| | (2BA-2-DMHA) |
| Cytokines: | Interferon-α |
| | Interferon-γ |
| | Tumor necrosis factor |
| Others: | |
| Isoprenylation inhibitors: | Lovastatin |
| Dopaminergic neurotoxins: | 1-methyl-4-phenylpyridinium ion |
| Kinase inhibitors: | Staurosporine |
| | Imatinib mesylate |
| Actinomycins: | Actinomycin D |
| | Dactinomycin |
| Bleomycins: | Bleomycin A2 |
| | Bleomycin B2 |
| | Peplomycin |

TABLE 1-continued

| | |
|---|---|
| Anthracyclines: | Daunorubicin |
| | Doxorubicin (adriamycin) |
| | Idarubicin |
| | Epirubicin |
| | Pirarubicin |
| | Zorubicin |
| | Mitoxantrone |
| MDR inhibitors | verapamil |
| $Ca^{2+}$ ATPase inhibitors: | Thapsigargin |

In other embodiments, the methods for treating or preventing cancer or neoplastic disease further comprise administering radiation therapy and/or one or more chemotherapeutic agents, in one embodiment where the cancer has not been found to be refractory. The Dipyrrole Compound can be administered to a patient that has also undergone surgery as treatment for the cancer.

In another specific embodiment, the invention provides a method to treat or prevent cancer that has shown to be refractory to treatment with a chemotherapy and/or radiation therapy.

In a specific embodiment, an effective amount of a Dipyrrole Compound is administered concurrently with chemotherapy or radiation therapy. In another specific embodiment, chemotherapy or radiation therapy is administered prior or subsequent to administration of a Dipyrrole Compound, such as at least an hour, five hours, 12 hours, a day or a week subsequent to or prior to administration of the Dipyrrole Compound.

If the Dipyrrole Compound is administered prior to administering chemotherapy or radiation therapy, the chemotherapy or radiation therapy is administered while the Dipyrrole Compound is exerting its therapeutic or prophylactic effect. If the chemotherapy or radiation therapy is administered prior to administering a Dipyrrole Compound, the Dipyrrole Compound is administered while the chemotherapy or radiation therapy is exerting its therapeutic effect.

The chemotherapeutic agents can be administered in a series of sessions, any one or a combination of the chemotherapeutic agents listed above can be administered. With respect to radiation therapy, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, may also be administered to expose tissues to radiation.

Additionally, the invention provides methods of treatment of cancer or neoplastic disease with a Dipyrrole Compound as an alternative to chemotherapy or radiation therapy where the chemotherapy or the radiation therapy has proven or may prove too toxic, e.g., results in unacceptable or unbearable side effects, for the patient being treated. The patient being treated with the present compositions may, optionally, be treated with other cancer treatments such as surgery, radiation therapy or chemotherapy, depending on which treatment is found to be acceptable or bearable.

5.10 Cancer and Neoplastic Disease Treatable or Preventable

Cancers or neoplastic diseases and related disorders that can be treated or prevented by administration of a Dipyrrole Compound include but are not limited to those listed in Table 2 (for a review of such disorders, see Fishman et al., 1985, *Medicine,* 2d Ed., J.B. Lippincott Co., Philadelphia):

TABLE 2

| CANCERS AND NEOPLASTIC DISORDERS |
|---|
| Leukemia |
|     acute leukemia |
|     acute t-cell leukemia |
|     acute lymphocytic leukemia |
|     acute myelocytic leukemia |
|         myeloblastic |
|         promyelocytic |
|         myelomonocytic |
|         Monocytic |
|     erythroleukemia |
|     chronic leukemia |
|     chronic myelocytic (granulocytic) leukemia |
|     chronic lymphocytic leukemia |
|     Hairy cell leukemia |
| Polycythemia vera |
| Lymphoma |
|     Hodgkin's disease |
|     non-Hodgkin's disease |
| Multiple myeloma |
| Waldenström's macroglobulinemia |
| Heavy chain disease |
| Myelodysplastic syndrome |
| Solid tumors |
|     sarcomas and carcinomas |
|         fibrosarcoma |
|         myxosarcoma |
|         liposarcoma |
|         chondrosarcoma |
|         osteogenic sarcoma |
|         chordoma |
|         angiosarcoma |
|         endotheliosarcoma |
|         lymphangiosarcoma |
|         lymphangioendotheliosarcoma |
|         synovioma |
|         mesothelioma |
|         Ewing's tumor |
|         leiomyosarcoma |
|         rhabdomyosarcoma |
|         colon carcinoma |
|         pancreatic cancer |
|         breast cancer |
|         ovarian cancer |
|         prostate cancer |
|         squamous cell carcinoma |
|         basal cell carcinoma |
|         adenocarcinoma |
|         sweat gland carcinoma |
|         sebaceous gland carcinoma |
|         papillary carcinoma |
|         papillary adenocarcinomas |
|         cystadenocarcinoma |
|         medullary carcinoma |
|         bronchogenic carcinoma |
|         renal cell carcinoma |
|         hepatoma |
|         bile duct carcinoma |
|         choriocarcinoma |
|         seminoma |
|         embryonal carcinoma |
|         Wilms' tumor |
|         cervical cancer |
|         uterine cancer |
|         testicular tumor |
|         lung carcinoma |
|         small cell lung carcinoma |
|         bladder carcinoma |
|         epithelial carcinoma |
|         glioma |
|         astrocytoma |
|         medulloblastoma |
|         craniopharyngioma |
|         ependymoma |

TABLE 2-continued

CANCERS AND NEOPLASTIC DISORDERS pinealoma
hemangioblastoma
acoustic neuroma
oligodendroglioma
meningioma
melanoma
neuroblastoma
retinoblastoma
Anal carcinoma
Rectal carcinoma
Cancer of unknown primary
Thyroid carcinoma
Gastric carcinoma
Head and Neck carcinomas
Non-small cell lung carcinoma In specific embodiments, cancer, malignancy or dysproliferative changes (such as metaplasias and dysplasias), or hyperproliferative disorders, are treated or prevented in the ovary, breast, colon, lung, skin, pancreas, prostate, bladder, or uterus. In other specific embodiments, sarcoma, melanoma, or leukemia is treated or prevented. In certain specific embodiments, the cancer to be treated is Acute Lymphoblastic Leukemia (ALL), Acute Myeloid Leukemia (AML), Acute Myeloid Leukemia/Other Myeloid Malignancies, Adrenocortical Carcinoma, AIDS-related Lymphoma, AIDS-related Malignancies, Alveolar Soft Part Sarcoma, Anal Cancer, Anaplastic Astrocytoma, Anaplastic Carcinoma, Thyroid, Angiosarcoma, Astrocytomas/Gliomas, Atypical Teratoid Rhabdoid Tumor, Basal Cell Carcinoma, Bile Duct Cancer, Bladder Cancer, Brain Stem Glioma (low grade and high grade), Burkitt's Lymphoma, Cancer of Unknown Primary (CUP), Carcinoid Tumor (gastrointestinal—usually appendix), Cervical Cancer, Childhood Leukemia, Childhood Hodgkin's Disease, Childhood Liver Cancer, Childhood Non-Hodgkin's Lymphoma, Childhood Rhabdomyosarcoma, Childhood Soft Tissue Sarcoma, Cholangiocarcinoma (cancer of the bile ducts), Chondromsarcoma, Chordoma, Choroid Plexus Tumors, includes choroid plexus carcinoma & papilloma, Chronic Myelogenous Leukemia (CML), Clear Cell Sarcoma, CNS Lymphoma, Colon Cancer, Craniopharyngiomas, Cutaneous T-Cell Lymphoma, Dermatofibrosarcoma Protuberans, Ductal Carcinoma—Invasive, Ductal Carcinoma in Situ (DCIS) (Non-invasive), Endometrial Cancer, Ependymoma, Epithelioid Sarcoma, Esophageal, Ewings Tumors and Primitive Neuroectodermal Tumors, Extraskeletal Chondrosarcoma, Extraskeletal Osteosarcoma, Fibrilary Astrocytoma, Fibrosarcoma, Follicular Carcinoma of Thyroid, Gallbladder Cancer, Gastric (stomach) Cancer, Gastrointestinal Stromal Tumor (GIST), Germ Cell Tumor, Germinoma, Germ Cell Tumor, Mixed Germ Cell Tumor, Gestational Trophoblastic Tumor (GTD) (placenta), Glioblastoma Multiformae (Also known as Astrocytoma Grade IV), Gliomas/Astrocytoma, Granular Cell Myoblastoma, Hairy Cell Leukemia, Hemangiosarcoma, Hepatobiliary, Hepatocellular (primary liver cancer), Hodgkin's Disease, Hurthle Cell Carcinoma of the Thyroid, Hypopharyngeal Cancer, Inflammatory Breast, Islet Cell Carcinoma (endocrine pancreas), Kaposi's Sarcoma, Kidney (Renal Cell) Cancer, Laryngeal Cancer, Leiomyosarcoma, Leukemia, Lip and Oral Cavity Cancer, Liposarcoma, Liver Cancer, Adult Primary (hepatocellular carcinoma), Liver cancer, Metastatic Lobular Carcinoma—Invasive, Lobular Carcinoma in Situ (LCIS) (Non-invasive), Lung Cancer, Lymphangiosaroma, Lymphoma, Male Breast Cancer, Malignant Fibrous Histiocytoma (MFH), Malignant Hemangiopericytoma, Malignant Mesenchymoma, Malignant Mesothelioma, Malignant Peripheral Nerve Sheath Tumor, Malignant Schwannoma, Malignant Thymoma, Medullary Carcinoma of the Thyroid, Medulloblastoma, Melanoma, Meningiomas, Mesenchymoma, Mesothelioma, Merkel Cell Carcinoma, Metastatic Cancer (may include lung, brain, spine, bone, lymph nodes, other), Multiple Myeloma/Plasma Cell Neoplasm, Mycosis Fungoides, Myelodysplastic Syndrome, Myeloproliferative Disorders, Nasopharyngeal Cancer, Neuroblastoma, Neurofibrosarcoma, Nipple (Paget's Disease of the Breast), Non-Hodgkin's Lymphoma (NHL), Non-Small Cell Lung, Oligodendroglioma, Oropharyngeal Cancer, Osteosarcoma, Ovarian Epithelial Cancer, Ovarian Germ Cell Tumor, Ovarian Low Malignant Potential Tumor, Pancreatic Cancer, Papillary Carcinoma of the Thyroid, Paranasal Sinus and Nasal Cavity Cancer, Parathyroid Cancer, Penile Cancer, Peripheral Neuroectodermal Tumors, Pheochromocytoma (adrenal cancer), Pilocytic Astrocytoma, Pineal Parenchymal Tumor, Pineal Tumors, includes Pineoblastoma, Pituitary Tumor, includes Pituitary Adenoma, Primitive Neuroectodermal Tumors (Ewing's family of tumors), Primitive Neuroectodermal Tumors, Supratentorial, Primary Central Nervous System Lymphoma (CNS Lymphoma), Prostate Cancer, Rectal Cancer, Renal Pelvis and Ureter Cancer, Transitional Cell, Retinoblastoma, Rhabdomyosarcoma, Salivary Gland Cancer, Schwannomas, Sezary Syndrome, Small Cell Lung, Small Intestine Cancer, Squamous Cell Neck Cancer, Stomach (Gastric) Cancer, Synovial sarcoma, T-Cell Lymphoma, Cutaneous, Testicular Cancer, Thyroid Cancer, Urethral Cancer, Uterine Sarcoma, Vaginal Cancer, Visual Pathway and Hypothalamic Glioma, Vulvar Cancer, Waldenström's Macroglobulinemia, Wilms' Tumor and Other Childhood Kidney Tumors.

In another embodiment, the Dipyrrole Compounds are used to treat or prevent cancers including prostate (more preferably hormone-insensitive), Neuroblastoma, Lymphoma (preferably follicular or Diffuse Large B-cell), Breast (preferably Estrogen-receptor positive), Colorectal, Endometrial, Ovarian, Lymphoma (preferably non-Hodgkin's), Lung (preferably Small cell), Cervical or Testicular (preferably germ cell).

In another embodiment, the Dipyrrole Compounds are used to inhibit the growth of a cell derived from a cancer or neoplasm such as prostate (more preferably hormone-insensitive), Neuroblastoma, Lymphoma (preferably follicular or Diffuse Large B-cell), Breast (preferably Estrogen-receptor positive), Colorectal, Endometrial, Ovarian, Lymphoma (preferably non-Hodgkin's), Lung (preferably Small cell), Cervical or Testicular (preferably germ cell).

In specific embodiments of the invention, the Dipyrrole Compounds are used to inhibit the growth of a cell, said cell being derived from a cancer or neoplasm in Table 2 or herein.

5.11 Demonstration of Inhibition of Viruses and Viral Infections

The Dipyrrole Compounds may be demonstrated to inhibit the replication or infectivity of a virus or a virus-infected cell in vitro or in vivo using a variety of assays known in the art, or described herein. In certain embodiments, such assays may use cells of a cell line, or cells from a patient. In specific embodiments, the cells may be infected with a virus prior to the assay, or during the assay. The cells may be contacted with a virus. In certain other embodiments, the assays may employ cell-free viral cultures.

In one embodiment, a Dipyrrole Compound is demonstrated to have activity in treating or preventing viral disease by contacting cultured cells that exhibit an indicator of a viral reaction (e.g., formation of inclusion bodies) in vitro with the Dipyrrole Compound, and comparing the level of the indicator in the cells contacted with the Dipyrrole Compound with the level of the indicator in cells not so contacted, wherein a lower level in the contacted cells indicates that the Dipyrrole Compound has activity in treating or preventing viral disease. Cell models that can be used for such assays include, but are not limited to, viral infection of T lymphocytes (Selin et al., 1996, J. Exp. Med. 183:2489-2499); hepatitis B infection of dedifferentiated hepatoma cells (Raney et al., 1997, J. Virol. 71:1058-1071); viral infection of cultured salivary gland epithelial cells (Clark et al., 1994, Autoimmunity 18:7-14); synchronous HIV-1 infection of $CD4^+$ lymphocytic cell lines (Wainberg et al., 1997, Virology 233:364-373); viral infection of respiratory epithelial cells (Stark et al., 1996, Human Gene Ther. 7:1669-1681); and amphotrophic retroviral infection of NIH-3T3 cells (Morgan et al., 1995, J. Virol. 69:6994-7000).

In another embodiment, a Dipyrrole Compound can be demonstrated to have activity in treating or preventing viral disease by administering a Dipyrrole Compound to a test animal having symptoms of a viral infection, such as characteristic respiratory symptoms in animal models, or which test animal does not exhibit a viral reaction and is subsequently challenged with an agent that elicits a viral reaction, and measuring the change in the viral reaction after the administration of the Dipyrrole Compound, wherein a reduction in the viral reaction or a prevention of the viral reaction indicates that the Dipyrrole Compound has activity in treating or preventing viral disease. Animal models that can be used for such assays include, but are not limited to, guinea pigs for respiratory viral infections (Kudlacz and Knippenberg, 1995, Inflamm. Res. 44:105-110); mice for influenza virus infection (Dobbs et al., 1996, J. Immunol. 157:1870-1877); lambs for respiratory syncytial virus infection (Masot et al., 1996, Zentralbl. Veterinarmed. 43:233-243); mice for neurotrophic virus infection (Barna et al., 1996, Virology 223:331-343); hamsters for measles infection (Fukuda et al., 1994, Acta Otolaryngol. Suppl (Stockh.) 514:111-116); mice for encephalomyocarditis infection (Hirasawa et al., 1997, J. Virol. 71:4024-4031); and mice for cytomegalovirus infection (Orange and Biron, 1996, J. Immunol. 156:1138-1142). In certain embodiments of the invention more than one Dipyrrole Compound is administered to a test animal, virus, or viral-infected cell.

5.12 Viruses and Viral Infections

Viruses and viral infections that can be treated or prevented by administering a Dipyrrole Compound include but are not limited to those listed in Table 3 including, but not limited to, DNA viruses such as hepatitis type B and hepatitis type C virus; parvoviruses, such as adeno-associated virus and cytomegalovirus; papovaviruses such as papilloma virus, polyoma viruses, and SV40; adenoviruses; herpes viruses such as herpes simplex type I (HSV-I), herpes simplex type II (HSV-II), and Epstein-Barr virus; poxviruses, such as variola (smallpox) and vaccinia virus; and RNA viruses, such as human immunodeficiency virus type I (HIV-I), human immunodeficiency virus type II (HIV-II), human T-cell lymphotropic virus type I (HTLV-I), human T-cell lymphotropic virus type II (HTLV-II), influenza virus, measles virus, rabies virus, Sendai virus, picornaviruses such as poliomyelitis virus, coxsackieviruses, rhinoviruses, reoviruses, togaviruses such as rubella virus (German measles) and Semliki forest virus, arboviruses, and hepatitis type A virus.

In a one embodiment of the invention, the Dipyrrole Compounds are used to treat or prevent a viral infection associated with a virus as listed in Table 3. In another embodiment, the Dipyrrole Compounds are used to inhibit the replication or infectivity of a virus listed in Table 3. In yet another embodiment, the Dipyrrole Compounds are used to inhibit the growth of a cell infected with a virus listed in Table 3.

TABLE 3

| | |
|---|---|
| Herpesviruses: | EBV |
| | HHV-8 (KSHV) |
| | Herpesvirus saimiri |
| Adenoviruses: | All strains |
| Retroviruses: | HIV-1 and 2 |
| | HTLV-I |
| Human Papillomaviruses: | HPV - all strains |
| Birnaviruses: | Infectious pancreatic necrosis virus |
| Other: | African Swine Fever virus (all strains) |

Other anti-viral agents that can be used in combination with a Dipyrrole Compound include, but are not limited to, Cytovene, Ganciclovir, trisodium phosphonoformate, Ribavirin, d4T, ddI, AZT, and Amantadine, Rimandatine and other anti-influenza agents, Acyclovir, and related agents, Foscarnet and other anti-herpes virus agents.

5.13 Prodrugs

The present invention also encompasses the prodrugs of the Dipyrrole Compounds of the invention. Prodrugs of the Dipyrrole Compounds can be used with the methods of the invention. Further, prodrugs of the Dipyrrole Compounds can be formulated into pharmaceutical compositions of the invention.

The present invention also covers prodrugs of the Dipyrrole Compounds of the invention. Prodrugs include derivatives of Dipyrrole Compounds that can hydrolyze, oxidize, or otherwise react under biological conditions (in vitro or in vivo) to provide an active Dipyrrole Compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, and biohydrolyzable phosphate analogues. In certain embodiments, prodrugs of Dipyrrole Compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh). Biohydrolyzable moieties of a Dipyrrole Compounds 1) do not interfere with the biological activity of the compound but can confer upon that compound advantageous properties in vivo, such as uptake, duration of action, or onset of action; or 2) are biologically inactive but are converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

5.14 Screening Assays

The invention provides methods for screening for compounds that can be used in combination with a Dipyrrole Compound in the treatment of cancer, neoplastic disease, or viral infection. In certain embodiments, a Dipyrrole Compound of Formula (Ia) or (Ib) and a test compound are co-administered to an animal model system of a cancer, neoplastic disease, or viral infection. The anti-cancer, anti-neoplastic, or anti-viral effect of the combination of the Dipyrrole Compound and the test compound is then compared to the anti-cancer, anti-neoplastic, or anti-viral effect of the Dipyrrole Compound and the test compound individually. In certain aspects, a test compound is useful in combination with the Dipyrrole Compound for the treatment of cancer, a neoplastic disease, or a viral infection if it acts synergistically with the Dipyrrole Compound, i.e., if the anti-cancer, anti-neoplastic, or anti-viral effect of the combination of the Dipyrrole Compound and the test compound is greater than the added effects of Dipyrrole Compound and the test compound individually. In other aspects, a test compound is useful in combination with the Dipyrrole Compound for the treatment of cancer, a neoplastic disease, or a viral infection if its anti-cancer, anti-neoplastic, or anti-viral effect is additive to the anti-cancer, anti-neoplastic, or anti-viral effect of the Dipyrrole Compound but any negative side effects of the test compound and the Dipyrrole Compound are not additive such that the same anti-cancer, anti-neoplastic, or anti-viral effect can be reached with a lower risk of side effects.

In certain embodiments, a cancer cell is contacted with a Dipyrrole Compound of Formula (Ia) or (Ib) and a test compound to measure the combined effect of the Dipyrrole Compound with the test compound on cancer cell viability. Test compounds that act synergistically with the Dipyrrole Compound are useful for combination therapies with the Dipyrrole Compound. Further, test compounds whose anti-cancer cell effect is additive to the anti-cancer cell effect of the Dipyrrole Compound and that are less cytotoxic to non-cancerous cells than the Dipyrrole Compound alone are useful in combination therapies with the Dipyrrole Compound.

In other embodiments, a Dipyrrole Compound of Formula (Ia) or (Ib) and a test compound are added to a culture of cells and viruses to measure the combined effect of the Dipyrrole Compound with the test compound on ability of the virus to infect cells and to propagate. Test compounds that act synergistically with the Dipyrrole Compound are useful for combination therapies with the Dipyrrole Compound to treat infections with the virus. Further, test compounds whose anti-viral activity is additive to the anti-viral activity of the Dipyrrole Compound and that are less cytotoxic than the Dipyrrole Compound alone are useful in combination therapies with the Dipyrrole Compound.

Suitable compounds that can be used in combination with a Dipyrrole Compound in the treatment of viral infections can also be identified in animal models for viral infections by co-administering the Dipyrrole Compound and a test compound.

Any molecule can be used as a test compound in a screening assay of the invention. Exemplary test compounds are small organic molecules, DNA molecules, RNA molecules, sugars, lipids, or peptides. In certain embodiments, combinatorial libraries of different test compounds are used with the screening methods of the invention. To facilitate screening, test compounds can be screened in pools of at least 10, 50, 100, 500, 1000, 5000, 10000, 50000, or at least 100000 test compounds. To facilitate screening, test compounds can be screened in pools of at most 10, 50, 100, 500, 1000, 5000, 10000, 50000, or at most 100000 test compounds.

6. EXAMPLES

6.1 Example 1

Synthesis of Compound 22

Referring to Scheme 3, to a solution of the triflate (48) (10.0 g, 2.84 mmol) and 4-dimethylaminophenyl boronic acid (49) (0.928 gm, 5.69 mmol) in anhydrous dioxane (25 mL), 4M solution of $K_2CO_3$ (7.11 mL, 28.47 mmol) was added. The solution was degassed for 10 min and then tetrakis(triphenylphosophine) palladium (0) (33 mg, 0.028 mol) was added. The reaction mixture was heated at 90-95° C. for 3 hours. The reaction mixture was subsequently cooled to room temperature and was extracted with ethyl acetate. The organic layer was washed with brine and water. The organic layer was separated, dried over anhydrous sodium sulphate and filtered. The filtrate was evaporated to obtain a crude residue and which was purified by silica gel column chromatography to get the Compound 22 (0.713 g, 78%).

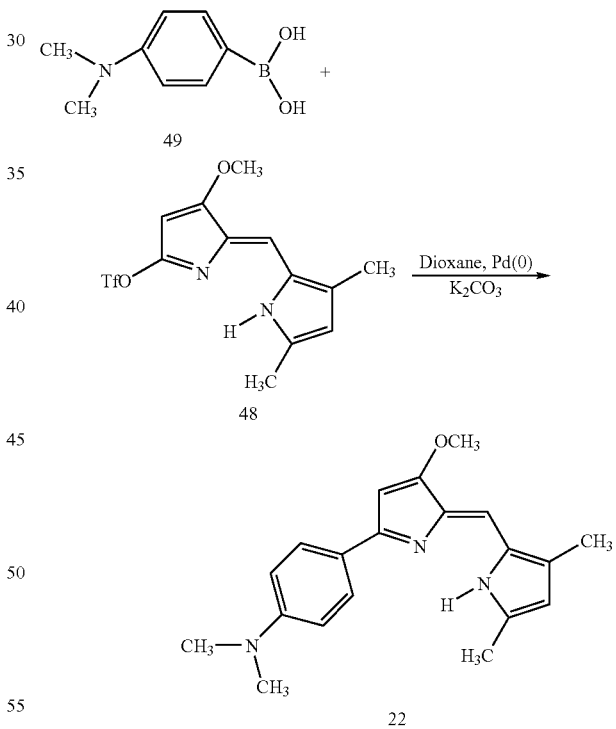

Scheme 3

6.2. Example 2

Synthesis of Compound 37

Referring to Scheme 4, to a solution of the triflate (48) (1.0 g, 2.84 mmol) and pyrazole boronic acid (50) [1-BENZYL-1H-PYRAZOL-4-YL-4-BORONIC ACID] (1.15 g, 5.69 mmol) in anhydrous dioxane (25 mL), 4M solution of $K_2CO_3$ (7.11 mL, 28.47 mmol) was added. The solution was degassed for 10 min and then tetrakis(triphenylphosophine) palladium (0) (33 mg, 0.028 mol) was added. The reaction mixture was heated at 90-95° C. for 3 hours. The reaction mixture was subsequently cooled to room temperature and was extracted with ethyl acetate. The organic layer was washed with brine and water. The organic layer was separated, dried over anhydrous sodium sulphate and filtered. The filtrate was evaporated to obtain a crude residue and which was purified by silica gel column chromatography to get the Compound 37 (0.726 g, 71%).

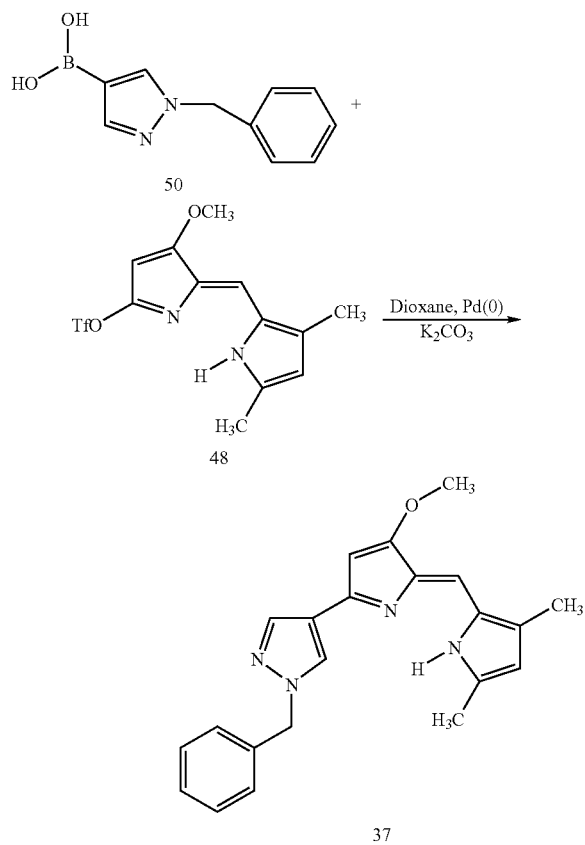

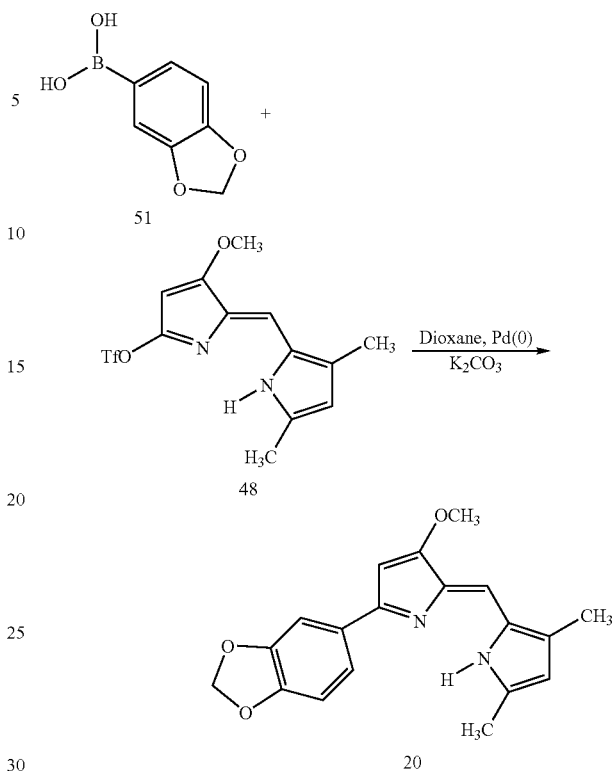

6.3. Example 3

Synthesis of Compound 20

Referring to Scheme 5, to a solution of the triflate (48, 1.0 g, 2.84 mmol) and 3-methelenedioxy phenyl boronic acid (51) (0.945 g, 5.69 mmol) in anhydrous dioxane (25 mL), 4M solution of $K_2CO_3$ (7.11 mL, 28.47 mmol) was added. The solution was degassed for 10 min and then tetrakis(triphenylphosophine) palladium (0) (33 mg, 0.028 mol) was added. The reaction mixture was heated at 90-95° C. for 3 hours. The reaction mixture was subsequently cooled to room temperature and was extracted with ethyl acetate. The organic layer was washed with brine and water. The organic layer was separated, dried over anhydrous sodium sulphate and filtered. The filtrate was evaporated to obtain a crude residue and which was purified by silica gel column chromatography to get the Compound 20 (0.624 g, 68%).

6.4 Example 4

Effects of Dipyrrole Compounds on Cancer Cell Viability in Cell Culture

To demonstrate the anti-oncogenic effect of Dipyrrole Compounds, their effect on cancer cell viability was demonstrated by measuring the cellular ATP levels before and after treating selected cell lines with Compounds of the invention. Selected cell lines included C33A cervical carcinoma cells and H1299 human non-small cell lung cancer-cells (American Type Culture Collection, Manassas, Va. USA), which were cultured in the media recommended by the American Type Culture Collection. The cells lines were plated in 96-well microtiter plates (PerkinElmer Life Sciences Inc, Boston, Mass., USA) at a confluency that allowed them to reach confluence after 4 days of growth. One day after plating, the cells were treated with various concentrations of Compounds. Stock solutions of the Compounds were prepared in dimethyl sulfoxide (Sigma-Aldrich Inc., St. Louis, Mo., USA), diluted in the recommended media and then added to the cells. The total dimethyl sulfoxide on the cells was 0.1%. After 3 days of incubation the ATP levels in the cells were quantified using a luminescent ViaLight detection system (Bio-Whittaker, MD, USA). The results were plotted relative to untreated control cells, which were set at a value of 100. The IC50s were determined using a best-fit sigmoidal dose response curve with variable slope.

As depicted in Table 4, these compounds were efficient in decreasing cellular ATP levels in H1299 and C33A cancer cell lines. Thus, these compounds are have utility in the methods of the invention, such as treatment and prevention of cancer and viral infections, respectively.

It should also be noted that for in vivo medicinal uses, potency is not the only factor to be considered to estimate the suitability of a compound as a pharmaceutical agent. Other factors such as toxicity and bioavailability also determine the suitability of a compound as a pharmaceutical agent. Toxicity and bioavailability can also be tested in any assay system known to the skilled artisan.

TABLE 4

| Compound | IC50 (µM) | |
|---|---|---|
| | H1299 | C33A |
| 1 | 10 | 10 |
| 2 | 10 | 2.5 |
| 3 | 10 | 3 |
| 4 | 16.6 | 16.6 |
| 5 | 10 | 2.2 |
| 6 | 8.5 | 6.5 |
| 7 | 15 | 9.5 |
| 8 | 10 | 8 |
| 9 | 21.6 | 10.6 |
| 10 | 4.6 | 3 |
| 11 | 12.5 | 7 |
| 12 | 14 | 15 |
| 13 | 40 | 2 |
| 14 | 6.5 | 0.7 |
| 15 | 6.6 | 0.75 |
| 16 | 4.5 | 3 |
| 17 | 0.58 | 0.21 |
| 18 | 4 | 2 |
| 19 | 20 | 20 |
| 20 | 0.55 | 0.21 |
| 21 | 1.34 | 0.69 |
| 22 | 0.42 | 0.29 |
| 23 | 7.55 | 1.6 |
| 24 | 1.056 | 0.503 |
| 25 | 16.51 | 7.748 |
| 26 | 3.648 | 0.849 |
| 27 | 6.259 | 6.996 |
| 28 | 2.379 | 0.627 |
| 29 | 6.644 | 1.150 |
| 30 | 5.688 | 1.2 |
| 31 | 0.668 | 0.212 |
| 32 | 6.872 | 6.330 |
| 33 | 15.882 | 8.727 |
| 34 | 1.241 | 1.227 |
| 35 | 15.902 | 8.961 |
| 36 | 1.427 | 1.185 |
| 37 | 1.647 | 0.181 |
| 38 | 6.69 | 2.0 |
| 39 | 20 | 7.648 |
| 40 | 20 | 8.548 |
| 41 | 10.103 | 4.174 |
| 42 | 13.91 | 7.9 |
| 43 | 0.709 | 0.131 |
| 44 | 8.297 | 2.164 |

6.5 Example 5

Effect of Compound 17 on Growth of Prostate Tumor Cells In Vivo

To demonstrate the antitumor activity of Compound 17 Mesylate Salt in vivo, experiments were conducted in SCID mice (Charles-River, Mass., USA) into which were injected human prostatic adenocarcinoma cancer PC3 cells. The resultant mice are a model for a human having prostatic cancer.

The human prostatic adenocarcinoma cancer PC3 cells were purchased from the American Type Culture Collection (ATCC). These cells were confirmed to be free of mycoplasma infection. Cells were maintained in the Roswell Park Memorial Institute (RPMI), supplemented with 10% inactivated fetal bovine serum and 1% penicillin-streptomycin-L-Glutamine, under 5% carbon dioxide ($CO_2$) at 37° C. For prostatic-tumor induction, cells were grown lower than 70% confluence in complete medium and then collected with trypsin (Bio Whittaker, Rockland, Me., USA). Cells were then centrifuged and washed 2 times in phosphate buffer solution (PBS) and resuspended in PBS at $1.5 \times 10^6$ cells/0.1 mL. PC3 cells were then transplanted subcutaneously into the right flank of SCID mice (Charles River Laboratories, Wilmington, Mass., USA), as a suspension of tumor cells ($1.5 \times 10^6$ cells in 100 µL PBS), under a laminar airflow hood. Eleven (11) days later, the size of each tumor was measured. When the average tumor volume reached approximately 20 mm³, the mice were randomized into groups of 10 mice each based on tumor size so that the average tumor size in each group was comparable. Relative tumor size and volume was calculated as follows: length (cm)×[width (cm)]²/2. There were four treatment groups of ten mice each: (a) a negative control group, (b) a positive control group and (c) a group treated with 36.25 µMoles/Kg of Compound 17 Mesylate Salt (d) a group treated with 72.5 µMoles/Kg of Compound 17 Mesylate Salt.

Treatments started on day eleven after PC3 cells transplantation. Compound 17 Mesylate Salt was administered intravenous (tail vein) injections once daily for five consecutive days at a dose of 36.25 µMoles/Kg or 72.5 µMoles/Kg. Compound 17 Mesylate Salt was prepared fresh daily in a vehicle solution of 9.6% polyethylene glycol 300, 0.4% polysorbate 20 and 5% dextrose. The negative control group was treated with vehicle alone. The injection volume for both the 72.5 µMoles/Kg Compound 17 Mesylate Salt treated group and the negative control group was 200 µl. The injection volume for the 36.25 µMoles/Kg Compound 17 Mesylate Salt treated group was 100 µl. The positive control group was treated once every 3 days for five times with cisplatin (Sigma, St. Louis, Mo., USA) at a dose of 3.5 mg/kg. Cisplatin was formulated in PBS on each day of the injection and was administered intraperitioneal (IP) in an injection volume of 70 µl.

The mice were weighed and the tumors measured on day 13 and every 2 days after treatment commenced. Observation continued for 32 days after initial tumor implantation. The changes in body weight and in the calculated tumor volume were plotted.

As shown in FIG. 1, mice treated with Compound 17 Mesylate Salt experienced a non-significant weight loss, whereas the cisplatin treated positive control group had a weight loss of 19% on day 27.

Figure 2:
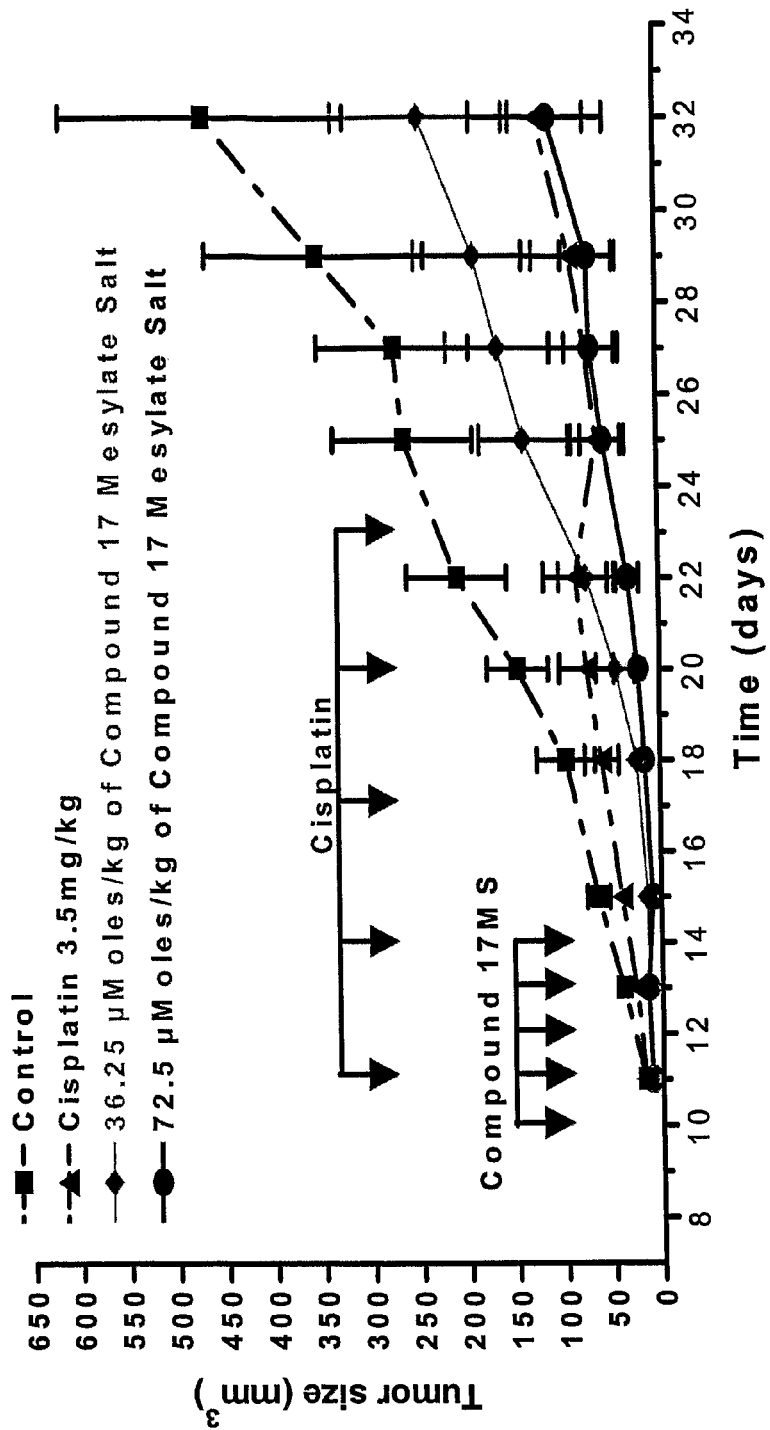
FIG. 2 illustrates the change in tumor volume in SCID mice which were implanted with human prostatic adenocarcinoma cancer PC3 cells and treated with cisplatin at a dose of 3.5 mg/kg or Compound 17 mesylate salt (MS) at a dose of 36.25 μMoles/kg or 72.5 μMoles/kg.

As shown in FIG. 2, Compound 17 Mesylate Salt treatment at a dose of 36.25 µMoles/Kg, once a day for five days, did not result in a statistical significant reduction in tumor growth compared to mice treated with vehicle only. The T/C values on days 29 and 32 were 53% and 52%, respectively. The treatment of Compound 17 Mesylate Salt at a higher dose of 72.5 µMoles/Kg, once a day for five days, resulted in a statistically significant (p<0.01) reduction in tumor growth compared to mice treated with vehicle only on days 29 and 32. The T/C values on days 29 and 32, for the group treated with Compound 17 Mesylate Salt treatment at a dose of 72.5 µMoles/Kg, were 18% and 22%, respectively.

As indicated in FIG. 2, Compound 17 Mesylate Salt at higher dosage significantly reduces the human prostate tumors implanted in SCID mice, an art-accepted model for human prostatic cancer. Accordingly, Compound 17 Mesylate Salt is useful for inhibiting the growth of prostate cancer and for treating or preventing prostate cancer in a patient, particularly a human patient.

6.6 Example 6

Effect of Compound 22 Mesylate Salt and Compound 37 Mesylate Salt on Growth of Cervical Tumor Cells In Vivo To demonstrate the antitumor activity of Compound 22 mesylate salt (MS) or Compound 37 mesylate salt (MS) in vivo, experiments were conducted in CB 17 SCID/SCID mice (Charles River, Mass., USA) into which were injected C33A human cervical cancer cells. The resultant mice are a model for a human having cervical cancer.

The C33A human cervical cancer cells were maintained in RPMI (Hyclone, Utah, USA) supplemented with 10% inactivated fetal bovine serum (Bio-Whittaker, MD, USA) and 1% penicillin-streptomycin-L-Glutamine (Gibco, N.Y., USA), under 5% $CO_2$ at 37° C., and passaged twice a week. The cells were grown at a confluency lower than 70% and than collected with Trypsin (Bio-Whittaker, MD, USA). The cells were then centrifuged and washed twice using phosphate buffered saline solution (PBS) and resuspended in PBS at $2\times10^6$ cells per 100 μl. Viability was examined by staining with trypan blue (Gibco, N.Y., USA) and only flasks with cell viability greater than 95% were used for in vivo studies.

C33A cells were injected subcutaneously into the flank of female CB17 SCID/SCID mice. Each mouse was inoculated with a suspension of $2\times10^6$ tumors cells per 100 μl on day zero. There were three treatment groups of ten mice each: (a) a negative control group, (b) a group treated with Compound 22 MS and (c) a group treated with Compound 37 MS.

Treatments started on day twenty eight after C33A cells transplantation. Compound 22 MS was administered intravenous (tail vein) injections once daily for five consecutive days at a dose of 10 mg/kg. Compound 37 MS was administered intravenous (tail vein) injections once daily for five consecutive days at a dose of 2.6 mg/kg. Both Compound 22 MS and Compound 37 MS were prepared fresh daily in a vehicle of 9.6% polyethylene glycol 300, 0.4% polysorbate 20 and 5% dextrose. The negative control group was treated with vehicle alone. The injection volume for Compound treated groups and the negative control group was 100 μl.

The mice were weighed and the tumors measured on day 28 and every 2 days after treatment commenced. Observation continued for 51 days after initial tumor implantation. The changes in body weight and in the calculated tumor volume were plotted.

Figure 3:
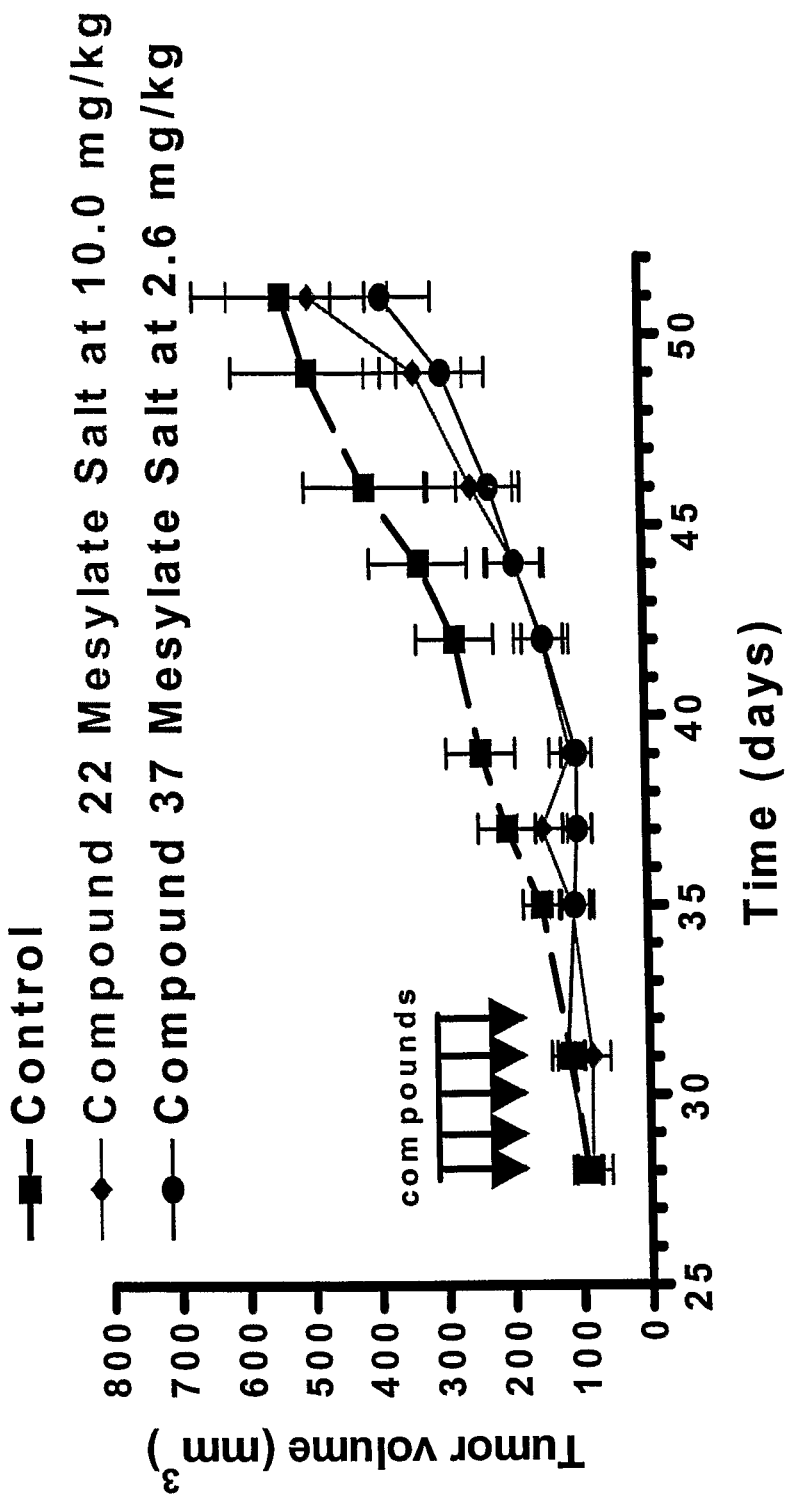
FIG. 3 illustrates the change in tumor volume in SCID mice which were implanted with C33A human cervical cancer cells and treated with Compound 22 mesylate salt (MS) at a dose of 10 mg/kg or Compound 37 mesylate salt (MS) at a dose of 2.6 mg/kg.

As shown in FIG. 3, Compound 22 MS treatment at a dose of 10 mg/kg once a day for five days resulted in a statistically significant (p=0.0024) reduction in tumor growth compared to mice treated with vehicle only. The T/C value on day 42 was 34%. As for Compound 37 MS treatment at a dose of 2.6 mg/kg once a day for five days resulted in a statistically significant (p<0.0001) reduction in tumor growth compared to mice treated with vehicle only. The T/C value on day 42 was 31%. On average, no significant changes in body weight were noted in any of the groups.

As indicated in FIG. 3, Compound 22 MS and Compound 37 MS significantly reduce the human cervical tumors implanted in SCID mice, an art-accepted model for human cervical cancer. Accordingly, Compound and Compound are useful for inhibiting the growth of cervical cancer and for treating or preventing cervical cancer in a patient, particularly a human patient.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A composition comprising a pharmaceutically acceptable carrier or vehicle and an effective amount of a compound having the formula

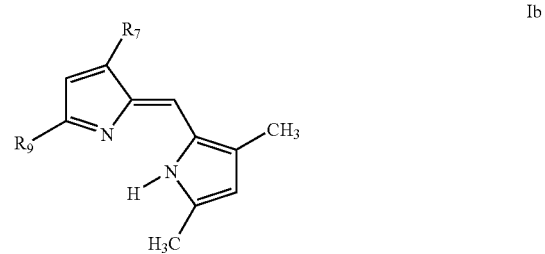

Ib or a pharmaceutically acceptable salt thereof,
wherein
$R_7$ is —O—($C_1$-$C_8$ alkyl);
$R_9$ is —($C_3$-$C_{12}$) cycloalkyl, -aryl selected from the group consisting of phenyl, tolyl, anthryl, fluorenyl, indenyl, azulenyl, phenanthryl, and naphthyl, each of which may be unsubstituted or substituted with one or more of halogen, OH, $C_{1-8}$ alkyl, O($C_{1-8}$ alkyl), $CH_2OR_{10}$, S($C_{1-8}$ alkyl), C(O)$R_{10}$, S(O)$_2R_{10}$, $NO_2$, or $SR_{10}$; —$C_1$-$C_{10}$ (aryl)alkyl, or substituted or unsubstituted 3- to 12-membered heterocycle selected from the group consisting of aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, oxazinyl, thiazinyl, diazinyl, triazinyl, tetrazinyl, imidazolyl, tetrazolyl, isoquinolinyl, quinolinyl, quinazolinyl, pyrrolidinyl, purinyl, isoxazolyl, benzisoxazolyl, furanyl, furazanyl, pyridinyl, oxazolyl, thiazolyl, thiophenyl, pyrazolyl, triazolyl, benzodiazolyl, benzotriazolyl, pyrimidinyl, isoindolyl, indazolyl, benzodioxole, dibenzofuran and dibenzothiophene, each of which may be substituted with one or more of halogen, O($C_{1-8}$ alkyl), or $C_{1-8}$ alkyl; and
each $R_{10}$ is independently —H, —$C_1$-$C_8$ alkyl, —$C_3$-$C_{12}$ cycloalkyl, —$C_2$-$C_8$ alkenyl, or —$C_2$-$C_8$ alkenyl.

2. The composition of claim 1, wherein $R_9$ is aryl selected from the group consisting of phenyl, tolyl, anthryl, fluorenyl, indenyl, azulenyl, phenanthryl, and naphthyl, each of which may be unsubstituted or substituted with one or more of halogen, OH, $C_{1-8}$ alkyl, O($C_{1-8}$ alkyl), $CH_2OR_{10}$, S($C_{1-8}$ alkyl), C(O)$R_{10}$, S(O)$_2R_{10}$, $NO_2$, or $SR_{10}$; or substituted or unsubstituted 3- to 12-membered heterocycle selected from the group consisting of aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, oxazinyl, thiazinyl, diazinyl, triazinyl, tetrazinyl, imidazolyl, tetrazolyl, isoquinolinyl, quinolinyl, quinazolinyl, pyrrolidinyl, purinyl, isoxazolyl, benzisoxazolyl, furanyl, furazanyl, pyridinyl, oxazolyl, thiazolyl, thiophenyl, pyrazolyl, triazolyl, benzodiazolyl, benzotriazolyl, pyrimidinyl, isoindolyl, indazolyl, benzodioxole, dibenzofuran and dibenzothiophene, each of which may be substituted with one or more of halogen, O($C_{1-8}$ alkyl), or $C_{1-8}$ alkyl.

3. The composition of claim 2, wherein $R_9$ is selected from the group consisting of substituted and unsubstituted phenyl, quinolinyl, thiophenyl, furyl, napthyl, pyridinyl, dihydrobenzofuranyl, pyrimidinyl, dihydrooxazinylphenyl, and pyrazolyl, each of which may be substituted with one or more of halogen, OH, $C_{1-8}$ alkyl, $O(C_{1-8}$ alkyl), $CH_2OR_{10}$, $S(C_{1-8}$ alkyl), $C(O)R_{10}$, $S(O)_2R_{10}$, $NO_2$, or $SR_{10}$.

4. The composition of claim 3, wherein the compound is selected from the group consisting of:
3-methoxy-2-((3,5-dimethyl-1H-pyrrol-2-yl)methylene)-5-phenyl-2H-pyrrole;
5-(4-chlorophenyl)-3-methoxy-2-((3,5-dimethyl-1H-pyrrol-2-yl)methylene)-2H-pyrrole;
2-((5-(2,4-difluorophenyl)-3-methoxy-2H-pyrrol-2-ylidene)methyl)-3,5-dimethyl-1H-pyrrole;
5-(4-methoxy-5-((3,5-dimethyl-1H-pyrrol-2-yl)methylene)-5H-pyrrol-2-yl)quinoline;
5-(4-fluorophenyl)-3-methoxy-2-((3,5-dimethyl-1H-pyrrol-2-yl)methylene)-2H-pyrrole;
2-((3-methoxy-5-(thiophen-2-yl)-2H-pyrrol-2-ylidene)methyl)-3,5-dimethyl-1H-pyrrole;
2-((5-(5-bromothiophen-2-yl)-3-methoxy-2H-pyrrol-2-ylidene)methyl)-3,5-dimethyl-1H-pyrrole;
N-4-(4-methoxy-5-((3,5-dimethyl-1H-pyrrol-2-yl)methylene)-5H-pyrrol-2-yl)-phenyl-methylsulfonamide;
4-(4-methoxy-5-((3,5-dimethyl-1H-pyrrol-2-yl)methylene)-5H-pyrrol-2-yl)benzaldehyde;
5-methoxy-2-(4-methoxy-5-((3,5-dimethyl-1H-pyrrol-2-yl)methylene)-5H-pyrrol-2-yl)benzaldehyde;
2-((3-methoxy-5-(3-nitrophenyl)-2H-pyrrol-2-ylidene)methyl)-3,5-dimethyl-1H-pyrrole;
2-((5-(furan-2-yl)-3-methoxy-2H-pyrrol-2-ylidene)methyl)-3,5-dimethyl-1H-pyrrole;
2-((5-(furan-3-yl)-3-methoxy-2H-pyrrol-2-ylidene)methyl)-3,5-dimethyl-1H-pyrrole;
2-((3-methoxy-5-(thiophen-3-yl)-2H-pyrrol-2-ylidene)methyl)-3,5-dimethyl-1H-pyrrole;
2-((3-methoxy-5-(2,4-dimethoxyphenyl)-2H-pyrrol-2-ylidene)methyl)-3,5-dimethyl-1H-pyrrole;
2-((3-methoxy-5-(3,4-dimethoxyphenyl)-2H-pyrrol-2-ylidene)methyl)-3,5-dimethyl-1H-pyrrole;
2-((3-methoxy-5-(2,3,4-trimethoxyphenyl)-2H-pyrrol-2-ylidene)methyl)-3,5-dimethyl-1H-pyrrole;
2-((3-methoxy-5-(2,5-dimethoxyphenyl)-2H-pyrrol-2-ylidene)methyl)-3,5-dimethyl-1H-pyrrole;
2-((5-(benzo[d][1,3]dioxol-5-yl)-3-methoxy-2H-pyrrol-2-ylidene)methyl)-3,5-dimethyl-1H-pyrrole;
2-((5-(4-(2-(pyrrolidin-1-yl)ethoxy)phenyl)-3-methoxy-2H-pyrrol-2-ylidene)methyl)-3,5-dimethyl-1H-pyrrole;
4-(4-methoxy-5-((3,5-dimethyl-1H-pyrrol-2-yl)methylene)-5H-pyrrol-2-yl)-N,N-dimethylbenzenamine;
2-((5-(2,3-dihydrobenzo[b][1,4]dioxin-7-yl)-3-methoxy-2H-pyrrol-2-ylidene)methyl)-3,5-dimethyl-1H-pyrrole;
2-((3-methoxy-5-(4-methoxy-3-methylphenyl)-2H-pyrrol-2-ylidene)methyl)-3,5-dimethyl-1H-pyrrole;
(4-(4-methoxy-5-((3,5-dimethyl-1H-pyrrol-2-yl)methylene)-5H-pyrrol-2-yl)phenyl)(pyrrolidin-1-yl)methanone;
2-((5-(3-fluoro-4-methoxyphenyl)-3-methoxy-2H-pyrrol-2-ylidene)methyl)-3,5-dimethyl-1H-pyrrole;
2-((3-methoxy-5-(2-methoxynaphthalen-6-yl)-2H-pyrrol-2-ylidene)methyl)-3,5-dimethyl-1H-pyrrole;
2-((3-methoxy-5-(3,4,5-trimethoxyphenyl)-2H-pyrrol-2-ylidene)methyl)-3,5-dimethyl-1H-pyrrole;
2-((5-(4-bromophenyl)-3-methoxy-2H-pyrrol-2-ylidene)methyl)-3,5-dimethyl-1H-pyrrole;
2-methoxy-3-(4-methoxy-5-((3,5-dimethyl-1H-pyrrol-2-yl)methylene)-5H-pyrrol-2-yl)pyridine;
2-((5-(2,3-dihydrobenzofuran-6-yl)-3-methoxy-2H-pyrrol-2-ylidene)methyl)-3,5-dimethyl-1H-pyrrole;
2,4-dimethoxy-5-(4-methoxy-5-((3,5-dimethyl-1H-pyrrol-2-yl)methylene)-5H-pyrrol-2-yl)pyrimidine;
2-chloro-3-(4-methoxy-5-((3,5-dimethyl-1H-pyrrol-2-yl)methylene)-5H-pyrrol-2-yl)pyridine;
3,4-dihydro-7-(4-methoxy-5-((3,5-dimethyl-1H-pyrrol-2-yl)methylene)-5H-pyrrol-2-yl)-4-methyl-2H-benzo[b][1,4]oxazine;
5-(4-methoxy-5-((3,5-dimethyl-1H-pyrrol-2-yl)methylene)-5H-pyrrol-2-yl)pyrimidine;
2-((5-(4-(isopropylthio)phenyl)-3-methoxy-2H-pyrrol-2-ylidene)methyl)-3,5-dimethyl-1H-pyrrole;
1-benzyl-4-(4-methoxy-5-((3,5-dimethyl-1H-pyrrol-2-yl)methylene)-5H-pyrrol-2-yl)-1H-pyrazole;
2-methoxy-5-(4-methoxy-5-((3,5-dimethyl-1H-pyrrol-2-yl)methylene)-5H-pyrrol-2-yl)phenol;
2-fluoro-5-(4-methoxy-5-((3,5-dimethyl-1H-pyrrol-2-yl)methylene)-5H-pyrrol-2-yl)pyridine;
2-fluoro-3-(4-methoxy-5-((3,5-dimethyl-1H-pyrrol-2-yl)methylene)-5H-pyrrol-2-yl)pyridine;
2-((5-(4-(tert-butoxymethyl)phenyl)-3-methoxy-2H-pyrrol-2-ylidene)methyl)-3,5-dimethyl-1H-pyrrole;
2-methoxy-5-(4-methoxy-5-((3,5-dimethyl-1H-pyrrol-2-yl)methylene)-5H-pyrrol-2-yl)pyridine;
3-(benzyloxy)-5-(3,4-dimethoxyphenyl)-2-((3,5-dimethyl-1H-pyrrol-2-yl)methylene)-2H-pyrrole; and
5-(benzo[d][1,3]dioxol-5-yl)-3-(benzyloxy)-2-((3,5-dimethyl-1H-pyrrol-2-yl)methylene)-2H-pyrrole.

5. A compound of the formula

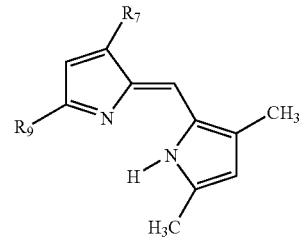

Ib or a pharmaceutically acceptable salt thereof,
wherein
$R_7$ is —O—$(C_1$-$C_8$ alkyl);
$R_9$ is —$(C_3$-$C_{12})$ cycloalkyl, -aryl selected from the group consisting of phenyl, tolyl, anthryl, fluorenyl, indenyl, azulenyl, phenanthryl, and naphthyl, each of which may be unsubstituted or substituted with one or more of halogen, OH, $C_{1-8}$ alkyl, $O(C_{1-8}$ alkyl), $CH_2OR_{10}$, $S(C_{1-8}$ alkyl), $C(O)R_{10}$, $S(O)_2R_{10}$, $NO_2$, or $SR_{10}$; —$C_1$-$C_{10}$ (aryl)alkyl, or substituted or unsubstituted 3- to 12-membered heterocycle selected from the group consisting of aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, oxazinyl, thiazinyl, diazinyl, triazinyl, tetrazinyl, imidazolyl, tetrazolyl, isoquinolinyl, quinolinyl, quinazolinyl, pyrrolidinyl, purinyl, isoxazolyl, benzisoxazolyl, furanyl, furazanyl, pyridinyl, oxazolyl, thiazolyl, thiophenyl, pyrazolyl, triazolyl, benzodiazolyl, benzotriazolyl, pyrimidinyl, isoindolyl, indazolyl, benzodioxole, dibenzofuran and dibenzothiophene, each of which may be substituted with one or more of halogen, $O(C_{1-8}$ alkyl), or $C_{1-8}$ alkyl; and each $R_{10}$ is independently —H, —$C_1$-$C_8$ alkyl, —$C_3$-$C_{12}$ cycloalkyl, —$C_2$-$C_8$ alkenyl, or —$C_2$-$C_8$ alkynyl.

6. The compound of claim 5 or a pharmaceutically acceptable salt thereof, wherein $R_9$ is aryl selected from the group consisting of phenyl, tolyl, anthryl, fluorenyl, indenyl, azulenyl, phenanthryl, and naphthyl, each of which may be unsubstituted or substituted with one or more of halogen, OH, $C_{1-8}$ alkyl, $O(C_{1-8}$ alkyl), $CH_2OR_{10}$, $S(C_{1-8}$ alkyl), $C(O)R_{10}$, $S(O)_2R_{10}$, $NO_2$, or $SR_{10}$, or substituted or unsubstituted 3- to 12-membered heterocycle selected from the group consisting of aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, oxazinyl, thiazinyl, diazinyl, triazinyl, tetrazinyl, imidazolyl, tetrazolyl, isoquinolinyl, quinolinyl, quinazolinyl, pyrrolidinyl, purinyl, isoxazolyl, benzisoxazolyl, furanyl, furazanyl, pyridinyl, oxazolyl, thiazolyl, thiophenyl, pyrazolyl, triazolyl, benzodiazolyl, benzotriazolyl, pyrimidinyl, isoindolyl, indazolyl, benzodioxole, dibenzofuran and dibenzothiophene, each of which may be unsubstituted or substituted with one or more of halogen, $O(C_{1-8}$ alkyl), or $C_{1-8}$ alkyl.

7. The compound of claim 5 or a pharmaceutically acceptable salt thereof, wherein $R_9$ is aryl selected from substituted and unsubstituted phenyl, anthryl, fluorenyl, indenyl, azulenyl, phenanthryl and naphthyl, each of which may be substituted with one or more of halogen, $O(C_{1-8}$ alkyl), or $C_{1-8}$ alkyl.

8. The compound of claim 5 or a pharmaceutically acceptable salt thereof, wherein $R_9$ is substituted or unsubstituted 3- to 12-membered heterocycle selected from the group consisting of substituted and unsubstituted aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, oxazinyl, thiazinyl, diazinyl, triazinyl, tetrazinyl, imidazolyl, tetrazolyl, isoquinolinyl, quinolinyl, quinazolinyl, pyrrolidinyl, purinyl, isoxazolyl, benzisoxazolyl, furanyl, furazanyl, pyridinyl, oxazolyl, thiazolyl, thiophenyl, pyrazolyl, triazolyl, benzodiazolyl, benzotriazolyl, pyrimidinyl, indazolyl, benzodioxole, dibenzofuran and dibenzothiophene, each of which may be substituted with one or more of halogen, $O(C_{1-8}$ alkyl), or $C_{1-8}$ alkyl.

9. The compound of claim 5 or a pharmaceutically acceptable salt thereof, wherein $R_9$ is selected from the group consisting of substituted and unsubstituted phenyl, quinolinyl, thienyl, furyl, napthyl, pyridinyl, dihydrobenzofuranyl, pyrimidinyl, dihydrooxazinylphenyl, and pyrazolyl, each of which may be substituted with one or more of halogen, OH, $C_{1-8}$ alkyl, $O(C_{1-8}$ alkyl), $CH_2OR_{10}$, $S(C_{1-8}$ alkyl), $C(O)R_{10}$, $S(O)_2R_{10}$, $NO_2$, or $SR_{10}$.

10. The compound of claim 9 or a pharmaceutically acceptable salt thereof, wherein $R_7$ is —$OCH_3$.

11. The compound of claim 5 or a pharmaceutically acceptable salt thereof, wherein $R_7$ is —$OCH_3$.

12. The compound of claim 5 or a pharmaceutically acceptable salt thereof, wherein $R_7$ is —O—($C_1$-$C_8$ alkyl) substituted with phenyl.

13. The compound of claim 12 or a pharmaceutically acceptable salt thereof, wherein $R_7$ is —O-benzyl.

14. The compound of claim 5, wherein the compound is selected from the group consisting of:

3-methoxy-2-((3,5-dimethyl-1H-pyrrol-2-yl)methylene)-5-phenyl-2H-pyrrole;

5-(4-chlorophenyl)-3-methoxy-2-((3,5-dimethyl-1H-pyrrol-2-yl)methylene)-2H-pyrrole;

2-((5-(2,4-difluorophenyl)-3-methoxy-2H-pyrrol-2-ylidene)methyl)-3,5-dimethyl-1H-pyrrole;

5-(4-methoxy-5-((3,5-dimethyl-1H-pyrrol-2-yl)methylene)-5H-pyrrol-2-yl)quinoline;

5-(4-fluorophenyl)-3-methoxy-2-((3,5-dimethyl-1H-pyrrol-2-yl)methylene)-2H-pyrrole;

2-((3-methoxy-5-(thiophen-2-yl)-2H-pyrrol-2-ylidene)methyl)-3,5-dimethyl-1H-pyrrole;

2-((5-(5-bromothiophen-2-yl)-3-methoxy-2H-pyrrol-2-ylidene)methyl)-3,5-dimethyl-1H-pyrrole;

N-4-(4-methoxy-5-((3,5-dimethyl-1H-pyrrol-2-yl)methylene)-5H-pyrrol-2-yl)-phenyl-methylsulfonamide;

4-(4-methoxy-5-((3,5-dimethyl-1H-pyrrol-2-yl)methylene)-5H-pyrrol-2-yl)benzaldehyde;

5-methoxy-2-(4-methoxy-5-((3,5-dimethyl-1H-pyrrol-2-yl)methylene)-5H-pyrrol-2-yl)benzaldehyde;

2-((3-methoxy-5-(3-nitrophenyl)-2H-pyrrol-2-ylidene)methyl)-3,5-dimethyl-1H-pyrrole;

2-((5-(furan-2-yl)-3-methoxy-2H-pyrrol-2-ylidene)methyl)-3,5-dimethyl-1H-pyrrole;

2-((5-(furan-3-yl)-3-methoxy-2H-pyrrol-2-ylidene)methyl)-3,5-dimethyl-1H-pyrrole;

2-((3-methoxy-5-(thiophen-3-yl)-2H-pyrrol-2-ylidene)methyl)-3,5-dimethyl-1H-pyrrole;

2-((3-methoxy-5-(2,4-dimethoxyphenyl)-2H-pyrrol-2-ylidene)methyl)-3,5-dimethyl-1H-pyrrole;

2-((3-methoxy-5-(3,4-dimethoxyphenyl)-2H-pyrrol-2-ylidene)methyl)-3,5-dimethyl-1H-pyrrole;

2-((3-methoxy-5-(2,3,4-trimethoxyphenyl)-2H-pyrrol-2-ylidene)methyl)-3,5-dimethyl-1H-pyrrole;

2-((3-methoxy-5-(2,5-dimethoxyphenyl)-2H-pyrrol-2-ylidene)methyl)-3,5-dimethyl-1H-pyrrole;

2-((5-(benzo[d][1,3]dioxol-5-yl)-3-methoxy-2H-pyrrol-2-ylidene)methyl)-3,5-dimethyl-1H-pyrrole;

2-((5-(4-(2-(pyrrolidin-1-yl)ethoxy)phenyl)-3-methoxy-2H-pyrrol-2-ylidene)methyl)-3,5-dimethyl-1H-pyrrole;

4-(4-methoxy-5-((3,5-dimethyl-1H-pyrrol-2-yl)methylene)-5H-pyrrol-2-yl)-N,N-dimethylbenzenamine;

2-((5-(2,3-dihydrobenzo[b][1,4]dioxin-7-yl)-3-methoxy-2H-pyrrol-2-ylidene)methyl)-3,5-dimethyl-1H-pyrrole;

2-((3-methoxy-5-(4-methoxy-3-methylphenyl)-2H-pyrrol-2-ylidene)methyl)-3,5-dimethyl-1H-pyrrole;

(4-(4-methoxy-5-((3,5-dimethyl-1H-pyrrol-2-yl)methylene)-5H-pyrrol-2-yl)phenyl)(pyrrolidin-1-yl)methanone;

2-((5-(3-fluoro-4-methoxyphenyl)-3-methoxy-2H-pyrrol-2-ylidene)methyl)-3,5-dimethyl-1H-pyrrole;

2-((3-methoxy-5-(2-methoxynaphthalen-6-yl)-2H-pyrrol-2-ylidene)methyl)-3,5-dimethyl-1H-pyrrole;

2-((3-methoxy-5-(3,4,5-trimethoxyphenyl)-2H-pyrrol-2-ylidene)methyl)-3,5-dimethyl-1H-pyrrole;

2-((5-(4-bromophenyl)-3-methoxy-2H-pyrrol-2-ylidene)methyl)-3,5-dimethyl-1H-pyrrole;

2-methoxy-3-(4-methoxy-5-((3,5-dimethyl-1H-pyrrol-2-yl)methylene)-5H-pyrrol-2-yl)pyridine;

2-((5-(2,3-dihydrobenzofuran-6-yl)-3-methoxy-2H-pyrrol-2-ylidene)methyl)-3,5-dimethyl-1H-pyrrole;

2,4-dimethoxy-5-(4-methoxy-5-((3,5-dimethyl-1H-pyrrol-2-yl)methylene)-5H-pyrrol-2-yl)pyrimidine;

2-chloro-3-(4-methoxy-5-((3,5-dimethyl-1H-pyrrol-2-yl)methylene)-5H-pyrrol-2-yl)pyridine;

3,4-dihydro-7-(4-methoxy-5-((3,5-dimethyl-1H-pyrrol-2-yl)methylene)-5H-pyrrol-2-yl)-4-methyl-2H-benzo[b][1,4]oxazine;

5-(4-methoxy-5-((3,5-dimethyl-1H-pyrrol-2-yl)methylene)-5H-pyrrol-2-yl)pyrimidine;

2-((5-(4-(isopropylthio)phenyl)-3-methoxy-2H-pyrrol-2-ylidene)methyl)-3,5-dimethyl-1H-pyrrole;

1-benzyl-4-(4-methoxy-5-((3,5-dimethyl-1H-pyrrol-2-yl)methylene)-5H-pyrrol-2-yl)-1H-pyrazole;

2-methoxy-5-(4-methoxy-5-((3,5-dimethyl-1H-pyrrol-2-yl)methylene)-5H-pyrrol-2-yl)phenol;

2-fluoro-5-(4-methoxy-5-((3,5-dimethyl-1H-pyrrol-2-yl)methylene)-5H-pyrrol-2-yl)pyridine;

2-fluoro-3-(4-methoxy-5-((3,5-dimethyl-1H-pyrrol-2-yl)methylene)-5H-pyrrol-2-yl)pyridine;

2-((5-(4-(tert-butoxymethyl)phenyl)-3-methoxy-2H-pyrrol-2-ylidene)methyl)-3,5-dimethyl-1H-pyrrole;

2-methoxy-5-(4-methoxy-5-((3,5-dimethyl-1H-pyrrol-2-yl)methylene)-5H-pyrrol-2-yl)pyridine;

3-(benzyloxy)-5-(3,4-dimethoxyphenyl)-2-((3,5-dimethyl-1H-pyrrol-2-yl)methylene)-2H-pyrrole;

5-(benzo[d][1,3]dioxol-5-yl)-3-(benzyloxy)-2-((3,5-dimethyl-1H-pyrrol-2-yl)methylene)-2H-pyrrole;

and pharmaceutically acceptable salts thereof.

15. The compound of claim 5, wherein the pharmaceutically acceptable salt is mesylate salt.

* * * * *

UNITED STATES PATENT AND TRADEMARK OFFICE
CERTIFICATE OF CORRECTION

PATENT NO. : 8,420,693 B2  
APPLICATION NO. : 11/794488  
DATED : April 16, 2013  
INVENTOR(S) : Attardo et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1315 days.

Signed and Sealed this
First Day of September, 2015

Michelle K. Lee
*Director of the United States Patent and Trademark Office*